United States Patent
Su et al.

(10) Patent No.: US 10,518,086 B2
(45) Date of Patent: Dec. 31, 2019

(54) SELECTIVE TERMINATION OF STIMULATION TO DELIVER POST-STIMULATION THERAPEUTIC EFFECT

(71) Applicant: Medtronic, Inc., Minneapolis, MN (US)

(72) Inventors: Xin Su, Plymouth, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 110 days.

(21) Appl. No.: 15/661,936

(22) Filed: Jul. 27, 2017

(65) Prior Publication Data

US 2017/0319849 A1 Nov. 9, 2017

Related U.S. Application Data

(63) Continuation of application No. 13/701,654, filed as application No. PCT/US2011/039315 on Jun. 6, 2011, now Pat. No. 9,724,509.

(Continued)

(51) Int. Cl.
*A61N 1/36* (2006.01)
*A61B 5/00* (2006.01)
(Continued)

(52) U.S. Cl.
CPC ...... *A61N 1/36007* (2013.01); *A61B 5/04882* (2013.01); *A61B 5/205* (2013.01);
(Continued)

(58) Field of Classification Search
CPC .............. A61N 1/36007; A61N 1/0514; A61B 5/04882; A61B 5/205; A61B 5/4836;
(Continued)

(56) References Cited

U.S. PATENT DOCUMENTS

| | | |
|---|---|---|
| 4,406,288 A | 9/1983 | Horwinski et al. |
| 5,919,216 A | 7/1999 | Houben et al. |

(Continued)

FOREIGN PATENT DOCUMENTS

| | | |
|---|---|---|
| WO | 2006092007 A1 | 9/2006 |
| WO | 2009045297 A1 | 4/2009 |
| WO | 2010123704 A2 | 10/2010 |

OTHER PUBLICATIONS

International Preliminary Report on Patentability from International Application No. PCT/US2011/039315, dated Dec. 20, 2012, 12 pp.

(Continued)

*Primary Examiner* — Carl H Layno
*Assistant Examiner* — Erin M Piateski
(74) *Attorney, Agent, or Firm* — Shumaker & Sieffert, P.A.

(57) ABSTRACT

In some examples, electrical stimulation is delivered to a patient such that selective termination of the stimulation causes a therapeutic effect in the patient after termination of the electrical stimulation to the patient. The electrical stimulation may be insufficient to produce a desired therapeutic effect in the patient during stimulation, but sufficient to induce a post-stimulation desired therapeutic effect following termination of the stimulation. In some examples, the electrical stimulation may be sub-threshold electrical stimulation. In some examples, the desired therapeutic effect may alleviate bladder dysfunction, bowel dysfunction, or other disorders. The stimulation may be selectively terminated in response to one or more therapy trigger events to induce the post-stimulation therapeutic effect.

24 Claims, 7 Drawing Sheets

Related U.S. Application Data

(60) Provisional application No. 61/352,179, filed on Jun. 7, 2010, provisional application No. 61/437,416, filed on Jan. 28, 2011.

(51) Int. Cl.
*A61B 5/0488* (2006.01)
*A61B 5/20* (2006.01)
*A61B 5/04* (2006.01)
*A61B 5/11* (2006.01)
*A61N 1/05* (2006.01)

(52) U.S. Cl.
CPC .......... *A61B 5/4836* (2013.01); *A61B 5/0031* (2013.01); *A61B 5/04001* (2013.01); *A61B 5/1116* (2013.01); *A61B 5/4047* (2013.01); *A61N 1/0514* (2013.01)

(58) Field of Classification Search
CPC . A61B 5/0031; A61B 5/04001; A61B 5/1116; A61B 5/4047
USPC .......................................................... 607/41
See application file for complete search history.

(56) References Cited

U.S. PATENT DOCUMENTS

| | | | |
|---|---|---|---|
| 5,984,854 | A | 11/1999 | Ishikawa et al. |
| 6,141,587 | A | 10/2000 | Mower |
| 6,393,323 | B1 | 5/2002 | Sawan et al. |
| 7,689,276 | B2 | 3/2010 | Dobak |
| 2003/0100930 | A1 | 5/2003 | Cohen et al. |
| 2004/0162594 | A1 | 8/2004 | King |
| 2005/0065575 | A1 | 3/2005 | Dobak |
| 2006/0047325 | A1 | 3/2006 | Thimineur et al. |
| 2006/0122660 | A1 | 6/2006 | Boveja et al. |
| 2006/0161218 | A1 | 7/2006 | Danilov |
| 2006/0200205 | A1 | 9/2006 | Haller |
| 2007/0100387 | A1* | 5/2007 | Gerber .................. A61B 5/053 607/41 |
| 2007/0100388 | A1 | 5/2007 | Gerber |
| 2009/0054950 | A1 | 2/2009 | Stephens |
| 2009/0118777 | A1 | 5/2009 | Iki et al. |
| 2009/0131993 | A1 | 5/2009 | Rousso et al. |
| 2009/0138061 | A1* | 5/2009 | Stephens ............ A61N 1/36007 607/41 |
| 2009/0264955 | A1 | 10/2009 | Giftakis et al. |
| 2009/0264956 | A1 | 10/2009 | Rise et al. |
| 2009/0264957 | A1 | 10/2009 | Giftakis et al. |
| 2009/0264967 | A1 | 10/2009 | Giftakis et al. |
| 2009/0306460 | A1 | 12/2009 | Stephens et al. |
| 2010/0076254 | A1 | 3/2010 | Jimenez et al. |

OTHER PUBLICATIONS

International Search Report and Written Opinion of International application No. PCT/US2011/039315, dated May 3, 2012, 17 pp.
Prosecution History from U.S. Appl. No. 13/701,654, dated Dec. 3, 2012 through Mar. 30, 2017, 98 pp.
Prosecution History from U.S. Appl. No. 13/701,603, dated Dec. 3, 2012 through Jan. 28, 2015, 85 pp.

* cited by examiner

SELECTIVE TERMINATION OF STIMULATION TO DELIVER POST-STIMULATION THERAPEUTIC EFFECT

This application is a continuation of U.S. patent application Ser. No. 13/701,654, filed Dec. 3, 2012, now U.S. Pat. No. 9,724,509, issued Aug. 8, 2017, which is a National Stage application under 35 U.S.C. § 371 of International Application No. PCT/US11/039315, filed on Jun. 6, 2011, which claims the benefit of U.S. Provisional Patent Application No. 61/352,179, filed on Jun. 7, 2010, and U.S. Provisional Patent Application No. 61/437,416, filed on Jan. 28, 2011. The entire contents of application Ser. No. 13/701,654, PCT/US11/039315, 61/352,179, and 61/437,416 are incorporated herein by reference.

TECHNICAL FIELD

The disclosure relates to medical devices and, more particularly, medical devices that deliver electrical stimulation to a patient.

BACKGROUND

Bladder dysfunction, such as overactive bladder, urgency, or urinary incontinence, is a problem that may afflict people of all ages, genders, and races. Various muscles, nerves, organs and conduits within the pelvic floor cooperate to collect, store and release urine. A variety of disorders may compromise urinary tract performance, and contribute to an overactive bladder, urgency, or urinary incontinence. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence.

In some cases, urinary incontinence can be attributed to improper sphincter function, either in the internal urinary sphincter or external urinary sphincter. For example, aging can result in weakened sphincter muscles, which may cause incontinence. Nerves running though the pelvic floor stimulate contractility in the sphincter. An improper communication between the nervous system and the urethra or urinary sphincter can result in a bladder dysfunction, such as overactive bladder, urgency, urge incontinence, or another type of urinary incontinence.

SUMMARY

In general, the disclosure is directed to devices, systems, and techniques for delivering electrical stimulation to a patient such that selective termination of the stimulation causes a desired therapeutic effect in the patient after termination of the stimulation. The electrical stimulation is selected to induce a post-stimulation therapeutic effect after the stimulation is terminated. The electrical stimulation may be selected to be insufficient to cause the desired therapeutic effect during stimulation, e.g., such that the desired therapeutic effect may occur only after electrical stimulation is terminated. In some examples, the stimulation may be sub-threshold electrical stimulation. For example, the stimulation may be sub-threshold in the sense that it is insufficient to cause not only the desired therapeutic effect during stimulation but also insufficient to cause an acute physiological response, such as a motor response, patient perception response, a non-therapeutic effect, or a detected physiological effect such as nerve action potentials, during stimulation. However, the sub-threshold stimulation is selected to be sufficient to cause the desired therapeutic effect to occur after the stimulation is terminated. The stimulation may be selectively terminated, in some examples, in response to one or more therapy trigger events to cause the post-stimulation therapeutic effect. As one example, stimulation may be terminated in response to a patient request for therapy.

In one example, the disclosure is directed to a method that includes delivering an electrical stimulation to a patient, detecting a therapy trigger event, and terminating the electrical stimulation in response to the detected therapy trigger event to induce a desired therapeutic effect in the patient after the termination, wherein the electrical stimulation is selected to be insufficient to cause the desired therapeutic effect during the delivery of the electrical stimulation but sufficient to induce the desired therapeutic effect after the delivery of the electrical stimulation is terminated.

In another example, the disclosure is directed to a system that includes a stimulation delivery module configured to generate and deliver electrical stimulation to a patient and a control module configured to control the delivery of the electrical stimulation to the patient, detect a therapy trigger event, and terminate the electrical stimulation in response to the detected therapy trigger event to induce a desired therapeutic effect in the patient after the termination. The electrical stimulation is selected to be insufficient to cause the desired therapeutic effect during the delivery of the electrical stimulation but sufficient to induce the desired therapeutic effect after the delivery of the electrical stimulation is terminated.

In a further aspect, the disclosure is directed to a system that includes means for delivering an electrical stimulation to a patient, means for detecting a therapy trigger event, and means for terminating the electrical stimulation in response to the detected therapy trigger event to induce a desired therapeutic effect in the patient after the termination, wherein the electrical stimulation is selected to be insufficient to cause the desired therapeutic effect during the delivery of the electrical stimulation but sufficient to induce the desired therapeutic effect after the delivery of the electrical stimulation is terminated.

In another aspect, the disclosure is directed to an article of manufacture that includes a computer-readable storage medium, which can be non-transitory. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

DETAILED DESCRIPTION

Figure 1:
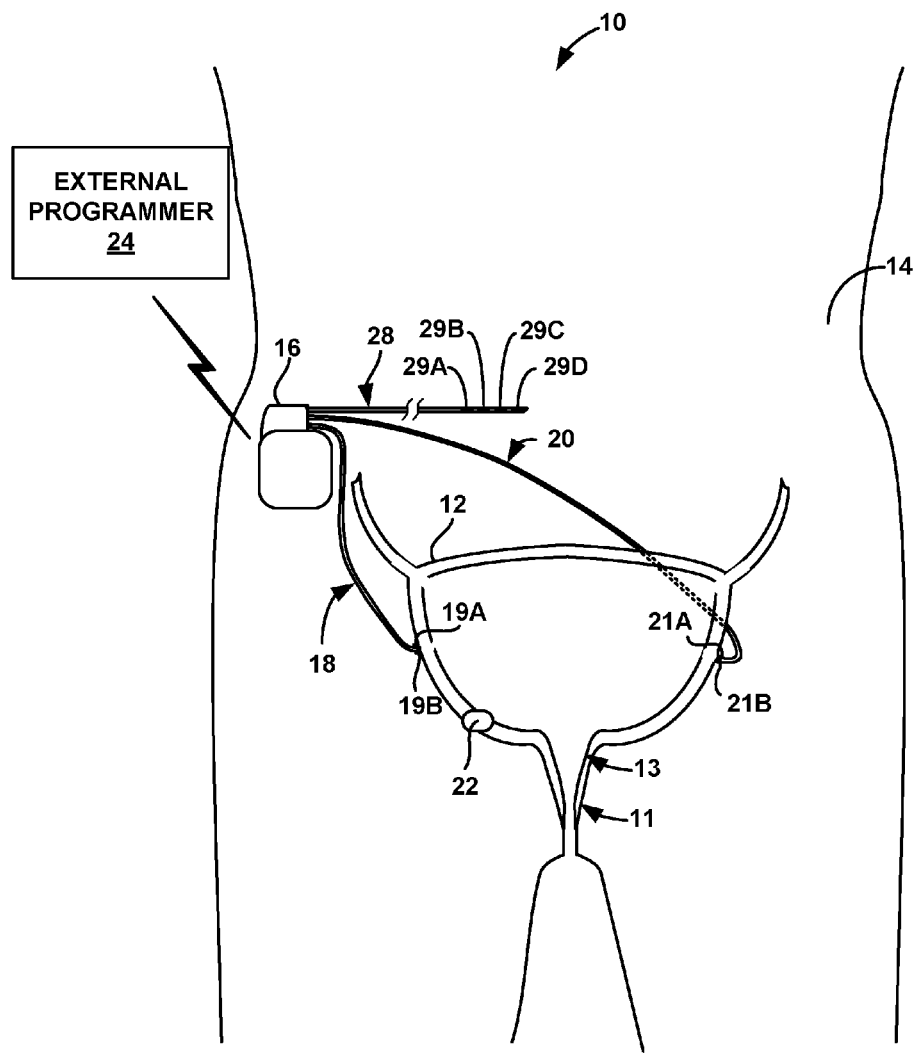
FIG. 1 is a conceptual diagram illustrating an example system that delivers electrical stimulation to a patient to manage bladder dysfunction, such as overactive bladder, urgency, or urinary incontinence, after termination of the stimulation.

The disclosure is directed to devices, systems, and techniques for delivering electrical stimulation to a patient such that selective termination of the stimulation causes a desired therapeutic effect in the patient after termination of the stimulation, i.e., a post-stimulation, desired therapeutic effect. The techniques may be used to provide therapy for a variety of dysfunctions, diseases or disorders. For purposes of illustration, but without limitation, use of the techniques will be described below with respect to bladder dysfunction. Some of the techniques described in this application may be related to or used in conjunction with techniques described in commonly assigned U.S. Provisional Patent Application Ser. No. 61/352,179, filed Jun. 7, 2010, entitled "Stimulation Therapy for Bladder Dysfunction," by Xin Su and Dwight E. Nelson.

Bladder dysfunction generally refers to a condition of improper functioning of the bladder or urinary tract, and may include, for example, an overactive bladder, urgency, or urinary incontinence. Overactive bladder is a patient condition that may include symptoms, such as urgency, with or without urinary incontinence. Urgency is a sudden, compelling urge to urinate, and may often, though not always, be associated with urinary incontinence. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence.

One type of therapy for treating bladder dysfunction includes delivery of electrical stimulation to a target tissue site within a patient to cause an acute therapeutic effect during delivery of the electrical stimulation. For example, delivery of electrical stimulation from an implantable medical device (IMD) to a target therapy site, e.g., a tissue site that delivers stimulation to modulate activity of a spinal nerve (e.g., a sacral nerve), a pudendal nerve, dorsal genital nerve, a tibial nerve, an inferior rectal nerve, a perineal nerve, or branches of any of the aforementioned nerves, may provide an immediate therapeutic effect for bladder dysfunction, such as a desired reduction in frequency of bladder contractions or increase in urinary sphincter contractions. In some examples, an acute therapeutic effect may be defined as a therapeutic effect that occurs within about 30 seconds or less (e.g., about 10 seconds) of the patient receiving the stimulation (e.g., the initiation of the stimulation). In some cases, electrical stimulation of the sacral nerve may modulate afferent nerve activities to restore urinary function during the electrical stimulation. This type of stimulation may be above a therapeutic intensity threshold, also referred to as a therapeutic threshold, in that it may have an intensity sufficient to cause an acute therapeutic effect during delivery of stimulation. In addition, the stimulation may be above a physiological intensity threshold, also referred to as a physiological threshold, in that it may be sufficient to cause, during delivery of stimulation, an acute physiological response such as a motor response, patient perception response, a non-therapeutic effect, or a detected physiological effect such as a sensed nerve action potential. In some examples, an acute response may be defined as a physiological response that occurs within about 30 seconds or less (e.g., about 10 seconds) of the patient receiving the stimulation (e.g., the initiation of the stimulation at the particular intensity level).

In contrast to this type of stimulation therapy, devices, systems, and techniques described in this disclosure are directed to delivering electrical stimulation to induce a desired therapeutic effect in the patient after terminating the delivery of electrical stimulation, i.e., after the electrical stimulation to the patient is turned off. In some cases, the stimulation parameter values are selected such that the desired therapeutic effect is observed within about 2 minutes to about 10 minutes, such as about 2 minutes to about 5 minutes, of the termination of the electrical stimulation to the patient. In some examples, such techniques may involve delivery of electrical stimulation that is below a therapeutic intensity threshold in that it is insufficient to cause a desired therapeutic effect during delivery of stimulation. However, the stimulation is sufficient to cause the desired therapeutic effect after the stimulation is terminated, i.e., as a post-stimulation therapeutic effect. In addition, in some examples, the electrical stimulation may be below a physiological threshold. If the stimulation is below a physiological threshold, the stimulation is insufficient to cause an acute physiological response during delivery of the stimulation. In other examples, the stimulation may be above the physiological intensity threshold. In each case, the electrical stimulation may be delivered to the patient, and then selectively terminated, to induce a post-stimulation, desired therapeutic effect in the patient after the electrical stimulation is terminated.

In some examples, the electrical stimulation that is below a therapeutic intensity threshold does not cause any significant therapeutic effect during stimulation. In other examples, however, the electrical stimulation may cause some detectable therapeutic effect during stimulation, but the therapeutic effect may be of a lesser magnitude than the desired therapeutic effect produced after termination of stimulation. This lesser therapeutic effect may be referred to as an ancillary therapeutic effect as it may be considered a side-effect or secondary effect that occurs when targeting the desired therapeutic effect that occurs after stimulation is terminated. As one example, if the desired therapeutic effect is a desired level of reduction in bladder contraction frequency, the stimulation may be insufficient to produce the desired therapeutic effect during stimulation if it causes no therapeutic effect in reducing bladder contraction frequency or if it causes a reduction in bladder contraction frequency that smaller than the desired level of reduction of bladder contraction frequency. In this example, the reduction in bladder contraction frequency may be greater in the post stimulation period compared to the stimulation period, when electrical stimulation is being delivered to the patient.

The sufficiency of the stimulation in producing a desired therapeutic effect may be a function of stimulation intensity and time for which stimulation is delivered. Stimulation intensity may be, in turn, a function of one or more parameters. In the case of stimulation pulses, stimulation intensity may be a function of current or voltage pulse amplitude, pulse rate, and pulse width. If the stimulation is delivered in pulse bursts, the intensity may also be a function of a duty cycle of the bursts. By configuring stimulation to have an intensity that is insufficient in intensity and/or time to cause the desired therapeutic effect during stimulation, yet sufficient in intensity and/or time to yield the desired therapeutic response after stimulation is terminated, it may be possible to deliver stimulation with reduced power consumption, reduced patient adaptation, and/or reduced side effects.

The desired therapeutic effect is different from the acute physiological response. As one illustration, the desired therapeutic effect may be a reduction in the frequency of bladder contractions in the patient, whereas the acute physiological response may be a motor response, patient perception response, a non-therapeutic effect, or a detected physiological effect such as a sensed nerve action potential. In some examples, the desired therapeutic effect may be desired in the sense that it may correspond to a desired degree of alleviation of bladder dysfunction versus no alleviation of the bladder dysfunction or a lesser degree of alleviation of the bladder dysfunction during delivery of electrical stimulation. Hence, the electrical stimulation may be selected such that the stimulation is sufficient to induce the desired therapeutic effect only after the electrical stimulation is terminated. In some examples, an ancillary therapeutic effect may be caused during stimulation, but to a degree less than the desired therapeutic effect produced after stimulation is terminated.

In summary, stimulation delivered according to some techniques described in this disclosure may be electrical stimulation insufficient to cause the desired therapeutic effect during stimulation, but sufficient to cause the desired therapeutic effect after stimulation is terminated. In some examples, the stimulation also may be insufficient to cause an acute physiological response, but sufficient to cause a desired therapeutic effect after stimulation is terminated. Selection of relatively low intensity stimulation that is insufficient to cause the desired therapeutic effect during stimulation may be desirable to reduce power consumption, patient adaptation, and/or undesirable side effects associated with higher intensity stimulation. Again, sufficiency of the stimulation may be a function of parameters such as the intensity and delivery time of the stimulation. Other parameters may include particular pulse rates or pulse widths that may be observed to support the desired therapeutic effect, e.g., independently of the contributions of pulse rate and pulse width to intensity. Accordingly, in some cases, it may be desired to adjust stimulation intensity by adjusting amplitude (e.g., current or voltage amplitude) while keeping pulse rate and/or pulse width in a range observed to be effective in supporting the therapeutic effect. For example, assuming a sufficient intensity, the therapeutic effect may be produced more effectively in some pulse rate or pulse width ranges than in other ranges.

Figure 9:
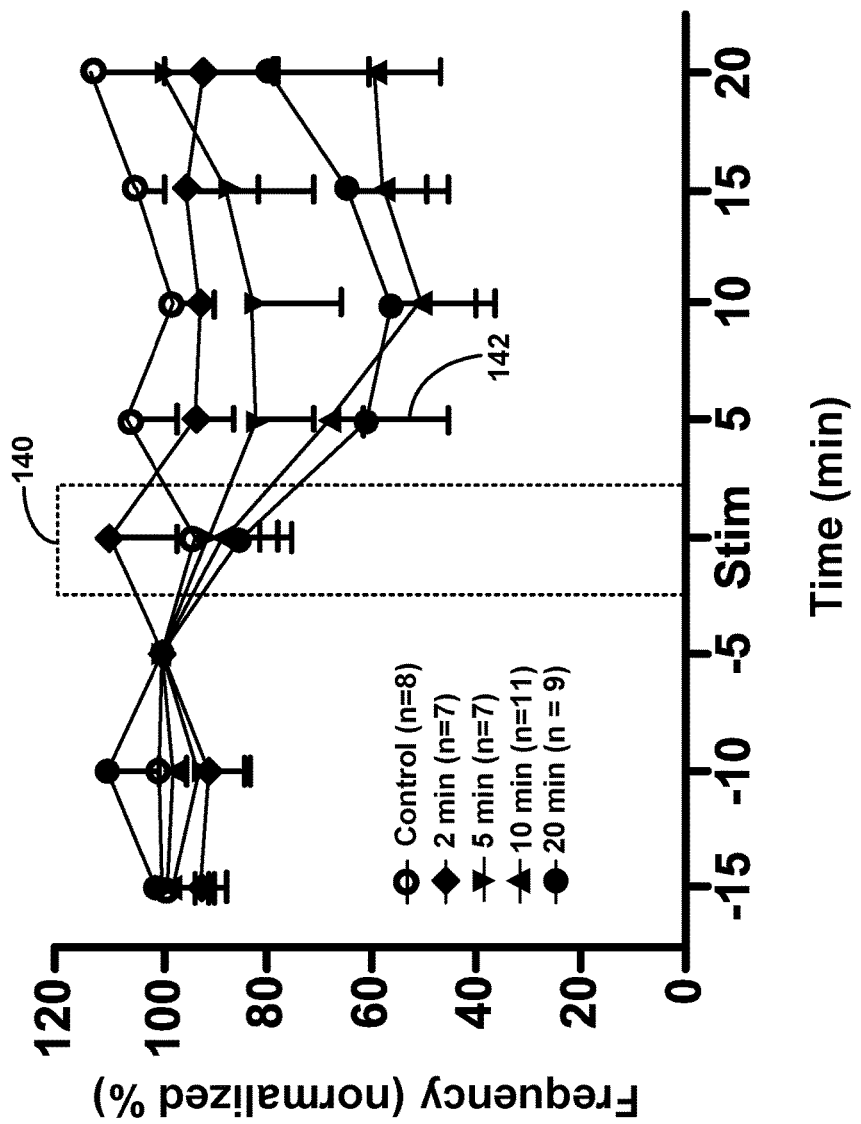
FIG. 9 is a graph that illustrates example changes in bladder contraction frequency in response to the termination of a sub-threshold electrical stimulation.

It has been observed in animal studies that substantial therapeutic effects may be induced after termination of electrical stimulation. For example, delivery of electrical stimulation has been observed to cause a reduction in bladder contraction frequency, as shown in FIG. 9 and described in further detail below, after stimulation is terminated. In particular, the rate of bladder contractions per unit time in animals under study has been observed to decrease after delivery of electrical stimulation is terminated. The delivered electrical stimulation may be low intensity stimulation that is insufficient to cause a therapeutic effect during the delivery of stimulation, but sufficient to induce a substantial, desired therapeutic effect once the stimulation was terminated. Accordingly, an IMD may be configured to generate electrical stimulation that induces a post-stimulation, desired therapeutic effect after stimulation is terminated. In one example, the IMD may deliver stimulation that is also insufficient to cause an acute physiological response during delivery of the stimulation, as well as post-stimulation, but still induces the desired therapeutic effect post-stimulation.

The electrical stimulation may be delivered by a stimulation delivery module and controlled by a control module contained within an IMD. The control module may control when the electrical stimulation begins and when the electrical stimulation is terminated. In some examples, the control module may selectively terminate the electrical stimulation upon the detection of a therapy trigger event. In particular, the control module may terminate the electrical stimulation in response to an event that triggers therapy. This therapy trigger event may include one or more different mechanisms that the control module may use to terminate the electrical stimulation. In one example, this therapy trigger event may be indicated by the expiration of a timer that defines the end of a time period, a particular time of day, or any other time-based event. In some examples, the timer can have a duration that is based on, for example, a micturition cycle of the patient. For example, the timer may be set such that the IMD terminates stimulation delivery at a certain period of time following the occurrence of the last voiding event of the patient. The period of time can be selected to be a time at which the bladder of the patient is expected to be at a particular fill level that increases the possibility of an involuntary voiding event or increases the patient's bladder contraction frequency, such that the therapeutic effects are desirable to reduce the possibility of an involuntary voiding event and/or the patient's bladder contraction frequency. In another example, alternatively or additionally, the therapy trigger event may be a request by the patient or other user for delivery of therapy. Upon this request for therapy, the electrical stimulation is terminated. Hence, a user request for therapy causes the IMD to terminate the delivered electrical stimulation so that the therapy to be provided. This is in contrast to an IMD that starts delivery of electrical stimulation in response to a user request for therapy.

In other examples, the control module may use one or more sensors to detect a physiological state of the patient and use the detected physiological state as a therapy trigger event. The physiological state may be utilized as an alternative or in addition to other therapy trigger events, such as those described above. This physiological state may be, for example, a bladder pressure, bladder contraction frequency, nerve activity, or any other physiological state indicative of bladder dysfunction. In each case, the sequence of events may be contrary to other types of stimulation therapy, where electrical stimulation is ordinarily started or increased in intensity in response to a request for therapy. In accordance with examples of this disclosure, electrical stimulation is actually terminated, rather than started, in order to induce the desired therapeutic effect.

In some examples, the control module may determine when to begin delivery of the electrical stimulation based on a desired therapy window, i.e., a window of time during which the desired therapeutic effect is to be provided. The therapy window may be a time period during which the patient may benefit from the desired therapeutic effect, such as a reduction in bladder contraction frequency. The target time and/or target duration of the desired therapy window may be calculated or estimated based on timing of prior incontinence episodes, a duration since the last voiding, or changes in sensed physiological states of the patient. The therapy trigger event may occur to specify the desired therapy window, such as the desired start and end times of the desired therapy window. In one example, a timer used as a therapy trigger event may be set such that the therapy window occurs at a predetermined time.

In some examples, instead of or in addition to the desired therapy window, a physiological state may be set as the therapy trigger event such that the desired therapy window may overlap with a physiological need by the patient for therapy. In some cases, the electrical stimulation may need to be delivered for at least several minutes before termination can induce the desired post-stimulation therapeutic effect. For this reason, the control module may be configured to start the electrical stimulation at a time that provides a sufficient amount of time before the desired therapy window such that termination will be capable of inducing the post-stimulation therapeutic effect during the therapy window. Alternatively, a patient may manually begin the electrical stimulation in anticipation of needing the post-stimulation therapeutic effect in a short time. In each case, the stimulation is delivered for a sufficient period of time in advance of the desired therapy window to support the desired, post-stimulation therapeutic effect.

The electrical stimulation may be targeted to manage bladder dysfunction, such as an overactive bladder, urgency, or urinary incontinence. For example, the stimulation may be delivered to target tissue sites normally used to alleviate these types of dysfunction. However, the stimulation may be configured to have a stimulation intensity, delivery time, or other characteristics that are insufficient to cause a desired therapeutic effect during stimulation but sufficient to induce the desired therapeutic effect after stimulation is terminated. In some examples, the stimulation may also be below a physiological threshold in the sense that the stimulation is insufficient to cause an acute physiological response during delivery of stimulation. Again, in some examples, the post-stimulation therapeutic effect may correspond to a desired degree of alleviation of dysfunction, such as a desired reduction in bladder contraction frequency, versus no alleviation or a lesser degree of alleviation of the dysfunction.

The IMD may implement the techniques described in this disclosure to deliver stimulation therapy to at least one nerve (e.g., spinal nerve or a pelvic floor nerve) to modulate activity of the nerve via at least one electrode electrically connected to the IMD. The electrical stimulation may induce a post-stimulation therapeutic effect, in some examples, in relation to the contraction of a detrusor muscle in a patient, which may cause a decrease in frequency of bladder contractions. Reduction in frequency of bladder contractions may reduce urgency of voiding and may reduce urgency and/or urinary incontinence, and thereby at least partially alleviate bladder dysfunction.

Although the techniques are primarily described in this disclosure for managing bladder dysfunction, the techniques may also be applied to manage other pelvic floor disorders or disorders relating to other organs, tissues or nerves of the patient. For example, the devices, systems, and techniques described in this disclosure alternatively or additionally may be utilized to manage sexual dysfunction, pelvic pain, fecal urgency or fecal incontinence. In the example of fecal incontinence, the IMD may deliver the electrical stimulation therapy upon detecting a physiological state indicative of an increased probability of an occurrence of a fecal incontinence (e.g., an increased patient activity level) and terminate the stimulation when the desired therapeutic effect may be used by the patient. The physiological state may include, for example, a magnitude of contraction of the anal sphincter, a patient activity level or a patient posture state. The IMD may use any suitable sensing mechanism to detect contraction of the anal sphincter, such as a pressure sensor or an EMG sensor.

FIG. 1 is a conceptual diagram illustrating an example therapy system 10 that delivers electrical stimulation to patient 14 to elicit a response from patient 14 that helps to manage bladder dysfunction, such as overactive bladder, urgency, or urinary incontinence after termination of the stimulation. As described above, system 10 may be configured to deliver electrical stimulation to the patient to induce a desired therapeutic effect in the patient only after the electrical stimulation is terminated. The electrical stimulation may be selected and delivered such that a desired therapeutic effect is induced in the patient after the electrical stimulation is terminated and not during stimulation. In some examples, the electrical stimulation may have an intensity that is below both a therapeutic threshold sufficient to produce the desired therapeutic effect during stimulation, and a physiological threshold sufficient to produce a physiological response during stimulation. However, the electrical stimulation may still be sufficient to cause the desired therapeutic effect after stimulation is terminated. In some examples, the electrical stimulation may induce a reduction in bladder contraction frequency that begins after termination of the electrical stimulation.

In the example of FIG. 1, therapy system 10 includes an implantable medical device (IMD) 16, which is coupled to leads 18, 20, and 28 and sensor 22. System 10 also includes an external programmer 24, which communicates with IMD 16 via wireless communication. IMD 16 generally operates as a therapy device that delivers electrical stimulation to, for example, a target tissue site proximate a spinal nerve, a sacral nerve, a pudendal nerve, dorsal genital nerve, a tibial nerve, an inferior rectal nerve, a perineal nerve, or other pelvic nerves, or branches of any of the aforementioned nerves. IMD 16 provides electrical stimulation to patient 14 by generating and delivering a programmable electrical stimulation signal (e.g., in the form of electrical pulses or an electrical waveform) to a target a therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect sense electrodes (e.g., electrodes 19A, 19B, 21A, and 21B) and stimulation electrodes, such as electrodes 29, to a sensing module and a stimulation delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases. In some examples, system 10 may include electrodes (such as electrodes 19 and 21), a strain gauge, one or more accelerometers, or any other sensor capable of detecting contractions of bladder 12 or any other indication of bladder dysfunction. In other examples, system 10 may not include electrodes 19 and 21 for sensing bladder volume.

One or more medical leads, e.g., leads 18, 20, and 28, may be connected to IMD 16 and surgically or percutaneously tunneled to place one or more electrodes carried by a distal end of the respective lead at a desired nerve or muscle site, e.g., one of the previously listed target therapy sites such as a tissue site proximate a spinal (e.g., sacral) or pudendal nerve. For example, lead 28 may be positioned such that electrodes 29 deliver electrical stimulation to a spinal, sacral or pudendal nerve to reduce a frequency of contractions of bladder 12. In addition, lead 28 may also deliver a secondary stimulation therapy to different nerves (e.g., a hypogastric nerve, a pudendal nerve, a dorsal penile/clitoral nerve, the urinary sphincter, or any combination thereof) to induce a post-stimulation therapeutic effect such as closure of a urinary sphincter of patient 14. For example, the post-stimulation therapeutic effect may reduce the frequency of bladder contractions, while the second stimulation therapy may promote sphincter closure to prevent urine leakage. Electrodes 29 of the common lead 28 may deliver stimulation to the same or different nerves. In FIG. 1, leads 18 and 20 are placed proximate to an exterior surface of the wall of bladder 12 at first and second locations, respectively. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects (e.g., therapeutic effects) after termination of the electrical stimulation. In examples, one or more of leads 18, 20, 28 may be, at least in part, paddle-shaped (e.g., a "paddle" lead), and may include an array of electrodes on a common surface, which may or may not be substantially flat.

In some examples, one or more of electrodes 19, 20, 29 may be cuff electrodes that are configured to extend at least partially around a nerve (e.g., extend axially around an outer surface of a nerve). Delivering electrical stimulation via one or more cuff electrodes and/or segmented electrodes may help achieve a more uniform electrical field or activation field distribution relative to the nerve, which may help minimize discomfort to patient 14 that results from the delivery of electrical stimulation. An electrical field may define the volume of tissue that is affected when the electrodes 19, 20, 29 are activated. An activation field represents the neurons that will be activated by the electrical field in the neural tissue proximate to the activated electrodes.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies or other electrical stimulations to respective stimulation sites within patient 14 or for monitoring at least one physiological parameter of patient 14.

In accordance with some examples of the disclosure, IMD 16 delivers electrical stimulation periodically over an extended period of time, e.g., chronic stimulation, to at least one of a spinal nerve (e.g., a sacral nerve), a pudendal nerve, dorsal genital nerve, a tibial nerve, an inferior rectal nerve, or a perineal nerve to provide a post-stimulation therapeutic effect after termination of the electrical stimulation. The desired therapeutic effect may be an inhibitory physiological response related to voiding of patient 14, such as a reduction in bladder contraction frequency by a desired level or degree (e.g., percentage). In particular, IMD 16 may deliver stimulation via at least one of electrodes 29 according to a stimulation program for a first time period sufficient to cause a post-stimulation, desired therapeutic effect during a second time period immediately following the first time period.

The stimulation program may define various parameters of the stimulation waveform and electrode configuration which result in a predetermined stimulation intensity being delivered to the targeted nerve. In some examples, the stimulation program defines parameters for at least one of a current or voltage amplitude of the stimulation signal, a frequency or pulse rate of the stimulation, the shape of the stimulation waveform, a duty cycle of the stimulation, a pulse width of the stimulation, and/or the combination of electrodes 29 and respective polarities of the subset of electrodes 29 used to deliver the stimulation. Together, these stimulation parameter values may be used to define the stimulation intensity (also referred to herein as a stimulation intensity level). In some examples, if stimulation pulses are delivered in bursts, a burst duty cycle also may contribute to stimulation intensity. Also, independent of intensity, a particular pulse width and/or pulse rate may be selected from a range suitable for causing the desired therapeutic effect after stimulation is terminated and, optionally, during stimulation. In addition to the above stimulation parameters, the stimulation may be defined by other characteristics, such as a time for which stimulation is delivered, a time for which stimulation is terminated and the time during which the post-stimulation therapeutic effect is produced, responsiveness of the stimulation to one or more therapy trigger events to terminate stimulation and thereby induce the desired therapeutic effect, or other characteristics.

The stimulation program may generally define stimulation selected to induce the desired therapeutic effect after stimulation is terminated but not during stimulation. In some examples, the program may also define stimulation with a stimulation intensity that is insufficient to cause an acute physiological response during stimulation, but is also sufficient to cause the desired therapeutic effect after stimulation is terminated. The desired therapeutic effect may refer to a desired degree of alleviation of bladder dysfunction. In some examples, it may be necessary for the stimulation to be delivered for at least a first period of time. The first period of time may be selected to be at least a minimum period of time sufficient to cause the post-stimulation, desired therapeutic effect during a second period of time immediately following the first period of time, and not more than a maximum period of time. The maximum period of time may be selected to be less than a time for which stimulation may cease to induce therapy upon termination. Alternatively, or additionally, the maximum period of time may be selected to be less than a period of time that may result in excessive power consumption or patient adaptation. Hence, the first period of time may be bounded by a minimum period of time necessary to cause the post-stimulation desired therapeutic effect and a maximum period of time associated with loss of the post-stimulation effect or excessive power consumption or adaptation.

The post-stimulation therapeutic effect may be related to voiding by patient 14. During this first period of time, in some examples, the electrical stimulation may cause substantially no therapeutic effect related to voiding by patient 14 during the delivery of the electrical stimulation. In other words, the therapeutic effect of patient 14 in relation to voiding during the first time period of the electrical stimulation may be substantially unchanged from the therapeutic effect of patient 14 prior to IMD 16 delivering any stimulation. In some examples, the therapeutic effect may comprise a reduction in contraction frequency of bladder 12. Accordingly, in some cases, a contraction frequency of bladder 12 may be substantially the same prior to delivery of the electrical stimulation and during the first time period during which electrical stimulation is delivered. However, the contraction frequency of bladder 12 may be reduced by a desired level after stimulation is terminated, i.e., as a desired post-stimulation therapeutic effect.

In other examples, the contraction frequency of bladder 12 may be reduced during the first time period compared to the contraction frequency of bladder 12 prior to IMD 16 delivering stimulation to patient 14. However, the amount, or magnitude, of the reduction during stimulation may be less than the amount of reduction desired for the therapeutic effect that results after stimulation is terminated, during the second period of time. In other words, in some examples, the electrical stimulation may cause no alleviation of dysfunction or some ancillary amount of alleviation, but not a degree of alleviation relative to that provided by the post-stimulation therapeutic effect. Hence, an ancillary therapeutic effect, or physiological response, arising during the electrical stimulation may not be a therapeutic effect similar to the desired therapeutic effect resulting once the electrical stimulation is terminated. In alternative examples, however, the stimulation may be selected to cause the desired therapeutic effect both during stimulation and post-stimulation.

The desired therapeutic effect may be any therapeutic effect that is anticipated to reach a desired, target efficacy level. In other words, the target efficacy level may be an efficacy level that a clinician or the patient wishes to reach after terminating the electrical stimulation. The target efficacy level may be determined based on previously detected therapeutic effect, a predetermined physiological state, physiological response, or a subjective indication from the patient. The target efficacy level of the desired therapeutic effect may be a parameter value or it may be a percentage of a previously identified value. For example, the target efficacy level of a reduction in bladder contraction frequency may be a 50 percent (%) reduction in the pre-stimulation bladder contraction frequency (e.g., the baseline bladder contraction frequency without intervention).

Although the desired therapeutic effect may not reach the target efficacy level, the target efficacy level may still be used to determine whether the therapeutic effect during stimulation is only an ancillary therapeutic effect. The ancillary therapeutic effect may be significantly less than the target efficacy level. For example, an ancillary therapeutic effect during the stimulation may be less than 20% of the target efficacy level. In an example where the target efficacy level is approximately a 50% reduction in the pre-stimulation contraction frequency, an ancillary therapeutic effect may be an effect that results in not more than a 10% reduction in pre-stimulation bladder contraction frequency (i.e., 20% of the target efficacy level of a 50% reduction). If the therapeutic effect is less than 20%, or some other predetermined percentage, of the target efficacy level of the desired therapeutic effect, then the therapeutic effect may not be considered to be a desired therapeutic effect.

As described above, the desired therapeutic effect induced after termination of stimulation may be substantially greater than any ancillary therapeutic effect during the delivery of the stimulation. Although the desired therapeutic effect may approximate the target efficacy level for post-stimulation therapy, the ancillary therapeutic effect may generally be less than 10% to 50% of the target efficacy level. In one example, the ancillary therapeutic effect may be less than approximately 20% of the target efficacy level. Therefore, any ancillary therapeutic effect caused by the electrical stimulation may not be the desired therapeutic effect for patient 14. Even though the electrical stimulation may cause a relatively insignificant ancillary therapeutic effect during stimulation, in some examples, the simulation may not cause any significant therapeutic effects during stimulation.

After the electrical stimulation is delivered for a first period of time and then terminated, a post-stimulation, desired therapeutic effect is induced during a second time period that immediately follows the first period of time. This desired therapeutic effect may be an inhibitory physiological response of patient 14 during the second time period during which no electrical stimulation is delivered to patient 14, such as a reduction in bladder contraction frequency, as described above. In some examples, the second time period may correspond to a lockout period in which IMD 16 is prevented from delivering any further electrical stimulation to patient 14. In other examples, IMD 16 may deliver a secondary electrical stimulation to bladder 12 or another tissue site in patient 14 during the second period of time without interfering with the post-stimulation therapeutic effect induced by the termination of the electrical stimulation delivered during the first period of time. The secondary electrical stimulation may or may not cause a secondary therapeutic effect during the second period. In other words, even if not all electrical stimulation is terminated after the first period, or a secondary stimulation occurs during the second period, the desired therapeutic effect may still be induced after termination of the electrical stimulation delivered during the first period of time.

In some examples, the first and second time periods may have durations on the order of minutes. For example, the first time period, during which IMD 16 delivers electrical stimulation, may be at least approximately 5 minutes, and may be between approximately 5 minutes and approximately 30 minutes. For example, the first time period may be at least approximately 10 minutes, and may be between approximately 10 minutes and approximately 20 minutes. Similarly, the second time period, after which IMD 16 has terminated the delivery of the electrical stimulation, may be at least approximately 5 minutes, and may be between approximately 5 minutes and approximately 30 minutes. In each case, in addition to the delivery time, the stimulation has an intensity level sufficient to cause the desired therapeutic effect after stimulation is terminated, but insufficient to cause the desired therapeutic effect during stimulation. The duration of the second period may be dependent upon the magnitude of the induced therapeutic effect. In some examples, the relative lengths of the first and second time periods may be selected to induce the desired therapeutic effect, balance the need of patient 14 for immediate therapeutic effects, and provide advantageous battery life to IMD 16 compared to an IMD 16 that delivers stimulation therapy substantially continuously.

Patient adaptation may generally refer to desensitization of the patient to the stimulation over time such the stimulation loses effect. Reduced stimulation intensity associated with delivery of electrical stimulation as described in this disclosure may reduce neuron habituation or other forms of patient adaptation to the stimulation therapy and extend an effective lifetime of the stimulation therapy (e.g., the time for which the stimulation therapy is efficacious in reducing bladder contraction frequency). It has been found that a patient may adapt to stimulation delivered by an IMD over time, such that a certain level of electrical stimulation provided to a tissue site in a patient may be less effective over time. As a result, beneficial effects of electrical stimulation may decrease over time for a patient. Although the electrical stimulation levels (e.g., amplitude of the electrical stimulation signal) may be increased to overcome such adaptation, the increase in stimulation levels may consume more power, and may eventually reach undesirable levels of stimulation, causing discomfort and/or a greater degree or acceleration of adaptation.

Generally, the stimulation program with which IMD 16 generates and delivers therapy to patient 14 may define a stimulation intensity. This stimulation intensity may be below a therapeutic intensity threshold, i.e., below a stimulation intensity that is sufficient to produce an acute therapeutic response (e.g., the desired therapeutic effect) during stimulation. However, the stimulation intensity below the therapeutic intensity threshold may still be sufficient to induce a therapeutic effect after termination of the stimulation. In some examples, this stimulation that does not cause an acute therapeutic response during stimulation (during the first period of time) may be above a physiological threshold stimulation intensity that still causes a motor response, a stimulation perception response, a non-therapeutic response, or a detected physiological response such as a nerve action potential.

The stimulation intensity that is below the therapeutic intensity threshold but still sufficient to induce a post-stimulation desired therapeutic effect may be determined experimentally for each patient. In one example, a clinician may begin the determination of the therapeutic intensity threshold with a relatively low intensity that is not likely to produce any acute physiologically significant response. Then, the clinician may incrementally increase one or more stimulation parameters, e.g., a current amplitude, pulse width, or pulse frequency, until an acute therapeutic response to the stimulation is detected. In one example, the clinician may select a pulse width and pulse frequency known to affect a specific tissue and incrementally increase the amplitude to increase stimulation intensity.

Once an acute therapeutic response is detected, such a particular percentage of reduction of bladder contraction frequency, these parameters may be used to define the therapeutic intensity threshold. From this determined therapeutic intensity threshold, the clinician may reduce one or more stimulation parameters such that the selected stimulation parameters produce an intensity that is below the therapeutic intensity threshold and insufficient to cause a desired therapeutic effect during the delivery of stimulation. The clinician may continue to reduce the intensity below the therapeutic threshold as long as the resulting stimulation parameters are still sufficient to induce a desired post-stimulation therapeutic effect, e.g., as observed upon delivery of stimulation to the patient with the parameters and then termination of the stimulation. In this manner, the clinician may select a lower intensity stimulation sufficient to support the post-stimulation therapeutic effect.

In other examples, the clinician may attempt to identify the lowest stimulation intensity possible that still induces a desired therapeutic effect after termination of the stimulation. However, as the stimulation intensity is lowered, the magnitude of the therapeutic effect observed after stimulation termination may likewise be reduced. In this manner, the post-stimulation therapeutic effect may be a graded effect that diminishes with lower stimulation intensities. At some specific low intensity, no post-stimulation therapeutic effect may be induced. In this manner, the clinician may experimentally determine the appropriate stimulation intensity that induces the desired therapeutic effect after termination.

In some examples, the stimulation intensity may also be set below a physiological response threshold sufficient to produce an acute physiological response during delivery of stimulation (during the first period of time). Accordingly, this electrical stimulation may be below the therapeutic threshold and below the physiological threshold. As mentioned above, the stimulation intensity may be a function of various parameters. In the case of stimulation pulses, the parameters may include a stimulation current or voltage pulse amplitude, pulse rate, pulse width, burst duty cycle, or other parameters.

A stimulation intensity below the physiological response threshold may be defined to be below the level at which an acute, physiologically significant response is first observed in patient 14 when increasing the stimulation intensity from a low intensity to a higher intensity. For example, the physiological threshold intensity may be defined as approximately the lowest stimulation intensity that causes an acute, physiologically significant effect in patient 14. In some examples, the physiological response may be different than the therapeutic response (e.g., an inhibitory physiological response) elicited by the delivery of electrical stimulation at the first stimulation intensity (or the second stimulation intensity, which is described below). This acute physiological response may be manifest in a number of different examples. For example, the acute physiological response may be a motor response, a stimulation perception response, or a detected physiological response such as a nerve action potential. These examples of an acute response may be defined as a physiological response that occurs within about 30 seconds or less (e.g., about 10 seconds) of patient 14 receiving the stimulation (e.g., the initiation of the stimulation at the particular intensity level). A stimulation perception response may be observed and reported by patient 14, e.g., as a paresthesia or other sensation. However, a motor response or a physiological response (e.g., a nerve impulse or non-therapeutic effect) may be reported by patient 14, observed by a clinician, or automatically detected by one or more sensors internal or external to patient 14. The acute, physiologically significant response may or may not be perceived by the patient.

Like the therapeutic intensity threshold, the physiological response threshold may be determined experimentally for each patient in order to determine parameters of the electrical stimulation. In one example, a clinician may begin the determination of the physiological threshold stimulation intensity with a relatively low intensity level that is not likely to produce any acute physiologically significant response. This relative intensity level may be selected, for example, based on the clinician's knowledge or based on other guidelines. The clinician can select the initial intensity by, for example, setting stimulation parameters (e.g., a current amplitude, a voltage amplitude, a frequency or pulse rate, a shape, a pulse width, a duty cycle, and/or the combination of electrodes) to produce a relatively low stimulation intensity and controlling IMD 16 to deliver stimulation to patient 14 using these parameters. Then, the clinician may incrementally increase one or more stimulation parameter values until an acute physiological response to the stimulation is detected. The stimulation parameter or parameters that are selected may be known to affect stimulation intensity and may include, for example, amplitude, pulse width and/or pulse rate. The process of modifying the stimulation parameter value and delivering stimulation according at the respective stimulation intensity level may be repeated until a threshold physiological response is observed (e.g., based on a signal generated by an implanted or external sensor or patient input indicating a perception of a physiological event). In this way, the process of finding the threshold intensity level may be an iterative procedure. Once an acute physiological response is detected, these parameters may be used to define the physiological threshold stimulation intensity.

From this determined threshold stimulation intensity, the clinician may reduce one or more stimulation parameters such that the selected stimulation parameters produce electrical stimulation having an intensity less than the physiological threshold stimulation intensity. The clinician may reduce the intensity to any value as long as the resulting stimulation parameters are still sufficient to induce the post-stimulation, desired therapeutic effect, e.g., as observed upon delivery of stimulation to the patient with the parameters and then termination of the stimulation.

In some examples, whether a response is physiologically significant may be defined by patient 14. As one example, the stimulation may cause movement of a toe of patient 14, and patient 14 may define the movement of the toe as physiologically significant when the movement of the toe is perceptible or when the movement of the toe is above some arbitrary amount defined by patient 14. In this manner, the physiological threshold stimulation intensity may be similar to a motor threshold that causes nerve fiber firing or muscle fiber firing. When stimulating one of the nerves described herein, such as a spinal nerve, sacral nerve, pudendal nerve, or the like, the physiological response may be a contraction of a toe of patient 14, a flexing of an anal sphincter of patient 14, or a detected signal on an electromyography (EMG). Other physiological responses may be detected when stimulating other nerves of patient 14.

In one example of determining the motor threshold, the physiological threshold stimulation intensity may be determined by setting the stimulation frequency at about 10 Hz to about 14 Hz and increasing the current amplitude until a muscle response is observed based on a sensor input (e.g., electromyogram (EMG) indicating the muscle movement) or patient input.

According to one example method, either the therapeutic intensity threshold or the physiological threshold stimulation intensity may be used as a convenient reference for a clinician to set the stimulation intensity level. Having determined the therapeutic intensity threshold or the physiological threshold stimulation intensity, the stimulation parameter values may be changed such that the electrical stimulation defines an intensity that is between about 50% and just less than about 100% of the selected threshold. This lower intensity may be used to deliver the electrical stimulation. In other examples, the stimulation intensity of the electrical stimulation may be less than about 50% of the selected threshold, or less than about 75% of the selected threshold. Any intensity below the selected threshold may be used provided the resulting electrical stimulation, upon delivery for a sufficient period of time, is still able to induce a desired therapeutic effect after the stimulation is terminated.

The stimulation intensity may be changed by adjusting at least one of the stimulation parameters described above, such as, for example, a current amplitude of the stimulation signal, a voltage amplitude of the stimulation signal, a frequency of the stimulation signal, a pulse rate of the stimulation signal, a pulse width of the stimulation signal, the shape of the stimulation signal, the duty cycle of the stimulation signal, or the combination of electrodes 29. For example, the current or voltage amplitude of the stimulation signal may be reduced to reduce an intensity of the stimulation. In particular, the stimulation may be selected to have an amplitude that is less than or equal to about 50%, or less than or equal to about 75%, or some other percentage, of an amplitude necessary to meet the therapeutic or physiological threshold, while pulse rate or pulse width are the same. In addition, or alternatively, the intensity may be selected based on percentages of pulse width, or pulse rate, or a combination of pulse width, pulse rate, and/or amplitude relative to the corresponding values associated with the therapeutic or physiological threshold. IMD 16 may generate and deliver the stimulation signal as substantially continuous waveforms or as a series of pulses.

As described above, the stimulation intensity may be determined by identifying parameter values associated with a therapeutic or physiological threshold stimulation intensity, and then selecting one or more parameter values of the stimulation such that the stimulation intensity is below one of the thresholds. In some examples, the stimulation intensity may be selected to be less than the therapeutic threshold intensity but greater than the physiological threshold intensity, or less than both the therapeutic threshold intensity and the physiological threshold intensity. In either case, a clinician may experimentally determine, by manipulation of one or more parameters, the appropriate stimulation intensity level at which the desired therapeutic effect does not occur during stimulation, but occurs after stimulation.

For example, after identifying an intensity level at which the desired therapeutic effect is no longer produced during stimulation, the clinician may continue to incrementally reduce the stimulation intensity level until the desired therapeutic effect is no longer produced post-stimulation, and then select a stimulation intensity that is above the level necessary to cause the post-stimulation, desired therapeutic effect. Alternatively, the clinician may incrementally increase the intensity level to identify a level sufficient to cause the post-stimulation, desired therapeutic effect but insufficient to cause the desired therapeutic effect during stimulation. Lower intensity levels may, in some examples, provide additional benefits in terms of power efficiency, patient adaptation, and reduced negative side effects.

In some examples, the first and second time periods pre- and post-stimulation may also be defined experimentally for each individual patient. For example, a clinician may deliver the determined electrical stimulation for a relatively short period of time, e.g., about five minutes, and then terminate the stimulation after the first period has elapsed. During the following second period, the clinician may observe patient 14 for the desired therapeutic effect. The clinician may incrementally increase the duration of the first period and observe the resulting, post-stimulation therapeutic effect for each of the first time period durations. Based on the most effective therapeutic effect, or based on a balance of most effective therapeutic effect, and power efficiency or patient adaptation considerations, the clinician may select the appropriate duration of the first time period. Although different durations for the first and second time periods may be evaluated in a clinic, patient 14 may leave the clinic and evaluate different durations and the resulting therapeutic effects using programmer 24. Patient 14 may then return to the clinic so that the most effective parameters are programmed for subsequent therapy.

In some examples, IMD 16 may deliver the stimulation therapy in an open loop manner, in which the first time period in which stimulation is delivered and the second time period in which stimulation is not delivered alternate periodically to define a therapy cycle. In some examples, each of the first time periods may be of substantially equal (e.g., equal) duration. Similarly, in some examples, each of the second time periods may be of substantially equal (e.g., equal) duration. However, the first time periods may be substantially equal (e.g., equal) or unequal to the second periods in other examples.

In other implementations, IMD 16 may deliver the electrical stimulation in a closed loop manner. For example, IMD 16 may sense contractions of bladder 12 during a time period prior to delivery of the electrical stimulation to establish a baseline contraction frequency of bladder 12 or the baseline contraction frequency may be stored in a memory of IMD 16 or another device (e.g., programmer 24). IMD 16 may sense contractions of bladder 12 via one or more sensing devices, such as, for example, electrodes 19 or 21, or sensor 22. IMD 16 may detect contractions of bladder 12 based on, for example, bladder impedance, bladder pressure, pudendal or sacral afferent nerve signals, a urinary sphincter EMG, or any combination thereof.

IMD 16 may utilize the sensed contractions of bladder 12 to determine a baseline contraction frequency of bladder 12, e.g., as a number of contractions of bladder 12 per unit time. The baseline contraction frequency of bladder 12 may represent the patient state when no therapeutic effects from delivery of stimulation by IMD 16 are present. In some cases, however, patient 14 may also receive other types of therapy for managing bladder dysfunction, such as a pharmaceutical agent. The baseline contraction frequency of bladder 12 may represent the patient state when patient 14 is under the influence of the pharmaceutical agent.

After determining a baseline contraction frequency, IMD 16 may sense, e.g., via electrodes 19 or 21 or sensor 22, bladder contractions or physiological parameters indicative of bladder contractions and determine a contraction frequency of bladder 12 during the second time period based on the sensed information, after the first time period during which IMD 16 delivers electrical stimulation to patient 14.

In some examples, IMD 16 may determine a contraction frequency of bladder 12 periodically throughout the second time period. During this monitoring of the physiological state of bladder 12, IMD 16 may compare the contraction frequency of bladder 12 during the second time period to the baseline contraction frequency or a threshold frequency that is based on the baseline contraction frequency.

The threshold frequency may be less than the baseline contraction frequency. In some examples, when the bladder contraction frequency sensed during the second time period is within a certain amount below the baseline contraction frequency or is above the threshold frequency, IMD 16 may initiate delivery of the electrical stimulation, e.g., to restart the first time period. In other examples, the second period of time may operate as a timer, similar to the first time period, such that the first and second time periods create a duty cycle. In this duty cycle, the end of the first time period may still be considered as a therapy trigger event.

Before IMD 16 may terminate the electrical stimulation to induce the post-stimulation therapeutic effect in patient 14, IMD 16 may detect a therapy trigger event that triggers the termination of the electrical stimulation. In other words, the trigger event that terminates stimulation occurs when therapy is to be delivered to patient 14, e.g., a therapeutic effect of the electrical stimulation therapy is desired. In this way, the therapy trigger event provides a stopping point for the delivered electrical stimulation. In the example of a duty cycle for the first and second time periods, the end of subsequent first time periods may also be considered to be a therapy trigger event. In this manner, a therapy trigger event may be a recurring time event within a therapy cycle.

As described above, in some examples, a therapy trigger event for terminating the electrical stimulation may be detected based on an elapsed time period (e.g., an expiration of the first time period), input from patient 14 requesting a therapeutic effect, or detecting a physiological state with sensor 22 or electrodes 19 and/or 21. The termination of the electrical stimulation may be initiated upon the detection of any of these example therapy trigger events.

IMD 16 can detect a contraction of bladder 12 using any suitable technique, such as based on a sensed physiological parameter. One example physiological parameter is an impedance of bladder 12. In the example shown in FIG. 1, IMD 16 may determine impedance of bladder 12 using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine impedance of bladder 12 based on the transmitted electrical signal. Such an impedance measurement may be utilized to determine response of contractions of bladder 12 during the electrical stimulation or after termination of the electrical stimulation, to determine a fullness of bladder 12, or the like. Although fullness may be a physiological state indicative of the need for the desired therapeutic effect, fullness may also indicate that the frequency of bladder contractions will increase to void bladder 12.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 19 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In other examples, electrodes 19 and 21 may be used to detect an EMG of the detrusor muscle. This EMG may be used to determine the frequency of bladder contractions and the physiological state of patient 14. The EMG may also be used to detect the strength of the bladder contractions in some examples. As an alternative, or in addition, to an EMG, a strain gauge or other device may be used to detect the status of bladder 12, e.g., by sensing forces indicative of bladder contractions.

In the example of FIG. 1, IMD 16 also includes a sensor 22 for detecting changes in the contraction of bladder 12. Sensor 22 may include, for example, a pressure sensor for detecting changes in bladder pressure, electrodes for sensing pudendal or sacral afferent nerve signals, electrodes for sensing urinary sphincter EMG signals (or anal sphincter EMG signals in examples in which system 10 provides therapy to manage fecal urgency or fecal incontinence), or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In some examples, IMD 16 may determine whether a contraction frequency of bladder 12 has occurred based on a pressure signal generated by sensor 22.

In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG; the sense electrodes may be carried on one of leads 18, 20, or 28 or additional leads coupled to IMD 16. In any case, in some examples, IMD 16 may control the timing of the delivery of the sub-threshold electrical stimulation based on input received from sensor 22.

Sensor 22 may comprise a patient motion sensor that generates a signal indicative of patient activity level or posture state. In some examples, IMD 16 may terminate the delivery of the electrical stimulation to patient 14 upon detecting a patient activity level exceeding a particular threshold based on the signal from the motion sensor. The patient activity level that is greater than or equal to a threshold (which may be stored in a memory of IMD 16) may indicate that there is an increase in the probability that an involuntary voiding event will occur, and, therefore, the therapeutic effects induced from the electrical stimulation may be desirable. In other examples, IMD 16 may use sensor 22 to identify posture states known to require the desired therapeutic effect. For example, patient 14 may be more prone to an involuntary voiding event when patient 14 is in an upright posture state compared to a lying down posture state.

In this manner, IMD 16 may control the delivery of the electrical stimulation by beginning the electrical stimulation once a particular activity level or posture state is detected such that the electrical stimulation may be delivered for a sufficient period of time before termination needed to induce the post-stimulation therapeutic effect. Conversely, if the electrical stimulation has already begun, IMD 16 may control the termination of the electrical stimulation to subsequently induce a post-stimulation therapeutic effect necessitated by the activity level or posture state of patient 14. In this way, the electrical stimulation provided by IMD 16 may be useful for reacting to the circumstances that may affect bladder dysfunction and plan ahead to provide therapy in response to these circumstances. In other examples, IMD 16 may deliver electrical stimulation for relatively long periods of time or continuously such that IMD 16 may be ready to terminate the stimulation at any time the therapeutic effect is needed, e.g., upon the detection of a trigger event.

In some examples, IMD 16 may anticipate or determine a desired therapy window for the post-stimulation therapeutic effect induced after termination of the electrical stimulation. The desired therapy window can define, for example, the duration of time the therapeutic effects of the electrical stimulation are observed (e.g., objectively, based on a sensed physiological signal) and/or perceived by patient 14. IMD 16 may utilize past rates of change in detected physiological states, e.g., bladder pressure, bladder contraction frequency, times of day in which patient 14 has requested therapy, or any other prior data related to the treatment of patient 14, to determine the duration and timing of the desired therapy window. Determining the desired therapy window may be useful because the electrical stimulation may need to be provided for several minutes or longer before termination of the stimulation will induce a post-stimulation, desired therapeutic effect. Accordingly, IMD 16 may begin the delivery of the electrical stimulation such that the first time period of electrical stimulation deliver expires prior to the therapy window and at a time that induces the therapeutic effect at the appropriate time to start the therapy window. For example, the therapy window may be a time of day that is associated with observed or detected physiological states. In addition, a clinician may program IMD 16 to set the therapy window based on daily patient activities.

In some examples, IMD 16 may also monitor one or more physiological states after termination of the electrical stimulation and update the stimulation parameters to maximize efficacy of the therapeutic effect. IMD 16 may adjust one or more stimulation parameters or select a new stimulation program based on the post-stimulation physiological states. For example, IMD 16 may determine that the desired therapeutic effect is not reaching the target efficacy level. IMD 16 may then change a voltage or current amplitude, pulse frequency, pulse width, electrode combination, or other stimulation parameter value in an attempt to maximize or at least increase the therapeutic effect for patient 14.

System 10 may also include an external programmer 24, as shown in FIG. 1. Programmer 24 may be a clinician programmer or patient programmer. In some examples, programmer 24 may be a wearable communication device, with a therapy request input integrated into a key fob or a wrist watch, handheld computing device, computer workstation, or networked computing device. Programmer 24 may include a user interface that is configured to receive input from a user (e.g., patient 14, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16. The user may also interact with a programmer to program IMD 16, e.g., select values for the stimulation parameter values with which IMD 16 generates and delivers stimulation and/or the other operational parameters of IMD 16, such as the duration of the first period of stimulation and the second period during which stimulation is not delivered.

For example, the user may use a programmer to retrieve information from IMD 16 regarding the contraction frequency of bladder 12 and/or voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected.

In some examples, patient 14 may interact with programmer 24 to control IMD 16 to deliver the electrical stimulation, e.g., to begin the stimulation in anticipation of a need for the post-stimulation therapeutic effects or terminate the simulation when the therapy is desired. Patient 14 may, for example, use a keypad or touch screen of programmer 24 to cause IMD 16 to deliver or terminate the electrical stimulation, such as when patient 14 senses that a leaking episode may be imminent. In this way, patient 14 may use programmer 24 to provide a therapy request to control the delivery of the electrical stimulation "on demand," e.g., when patient 14 deems the second stimulation therapy desirable. This request may be a therapy trigger event used to terminate electrical stimulation.

Accordingly, if electrical stimulation is being delivered at the time a therapy request is received, and stimulation has been delivered for a sufficient period of time to produce the post-stimulation, desired therapeutic effect, the stimulation may be terminated to deliver the post-stimulation therapeutic effect. It has been observed that it may be necessary to deliver electrical stimulation for at least some sufficient period of time in order for the desired therapeutic effect to be produced upon termination of stimulation. Therefore, if the electrical stimulation has not already been started, or has run for an insufficient period of time, a request for therapy may not be immediately on demand. Instead, patient 14 may need to wait for the electrical stimulation to be delivered for the first time period before termination of the stimulation can start the therapy by way of the post-stimulation therapeutic effect.

Programmer 24 may provide a notification to patient 14 when the electrical stimulation is being delivered or notify patient 14 of the prospective termination of the electrical stimulation. Because the electrical stimulation, in some examples, may be selected to be insufficient to produce the desired therapeutic effect when stimulation is being delivered to patient 14 (e.g., during the first period of time), e.g., insufficient to reduce frequency of bladder contractions by a desired amount, patent 14 may not be able to detect that stimulation is being delivered. In addition, notification of termination may be helpful so that patient 14 knows the desired therapeutic effect should be induced in the near term after termination, e.g., that the therapeutic effect is "armed" or in the processor of "arming" via delivery of the electrical stimulation for a first period of time sufficient to produce the post-stimulation therapeutic effect.

In such examples, programmer 24 may display a visible message, emit an audible alert signal or provide a somatosensory alert (e.g., by causing a housing of programmer 24 to vibrate). In other examples, the notification may indicate when therapy is available (e.g., a countdown in minutes, or indication that therapy is ready) such that immediate termination would induce the desired therapeutic effect. In this manner, programmer 24 may wait for input from patient 14 prior to terminating the electrical stimulation. Patient 14 may enter input that either confirms termination of the electrical stimulation so that the post-stimulation therapeutic effect is delivered or withholds termination until patient 14 needs the therapy.

In the event that no input is received within a particular range of time, programmer 24 may wirelessly transmit a signal that indicates the absence of patient input to IMD 16. IMD 16 may then elect to terminate stimulation or continue stimulation until the patient input is received based on the programming of IMD 16. As described herein, the termination or continuation of electrical stimulation may be responsive to other therapy trigger events.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
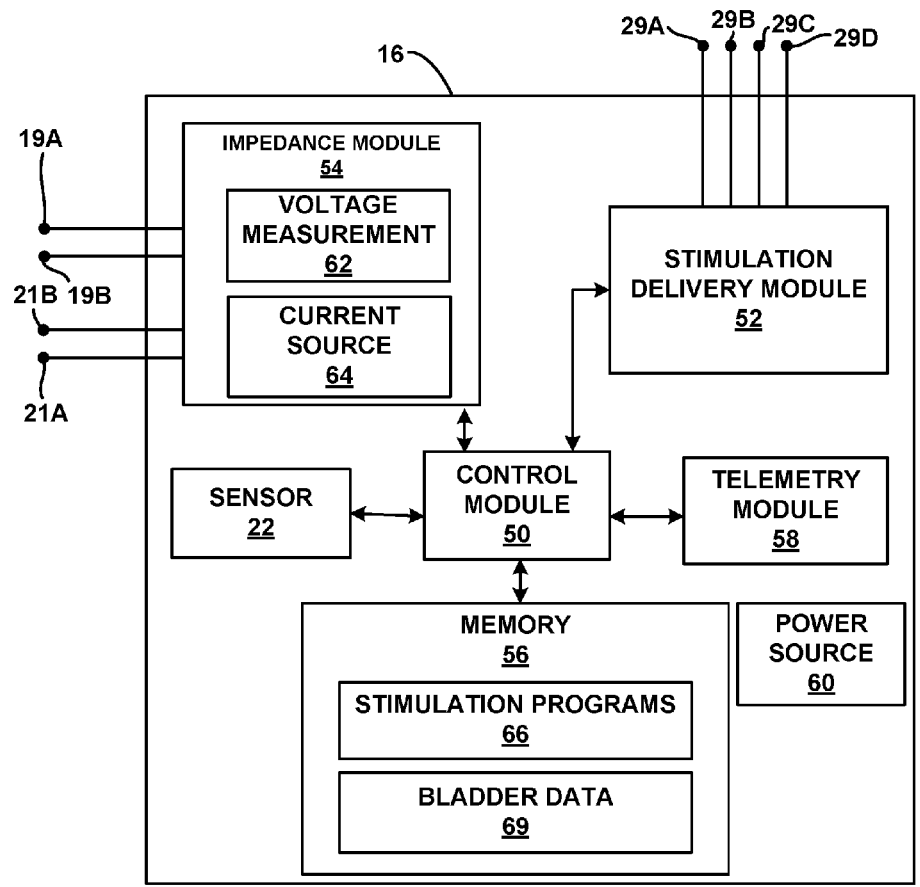
FIG. 2 is a block diagram illustrating an example configuration of an implantable medical device (IMD) which may be utilized in the system of FIG. 1.

FIG. 2 is a block diagram illustrating example components of IMD 16. In the example of FIG. 2, IMD 16 includes sensor 22, control module 50, stimulation delivery module 52, impedance module 54, memory 56, telemetry module 58, and power source 60. In other examples, IMD 16 may include a greater or fewer number of components. For example, in some examples, such as examples in which IMD 16 deliver the electrical stimulation in an open-loop manner, IMD 16 may not include sensor 22 and/or impedance module 54.

In general, IMD 16 may comprise any suitable arrangement of hardware, alone or in combination with software and/or firmware, to perform the techniques attributed to IMD 16 and control module 50, stimulation delivery module 52, impedance module 54, and telemetry module 58 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, in various examples, may include a memory 56, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although control module 50, stimulation delivery module 52, impedance module 54, and telemetry module 58 are described as separate modules, in some examples, control module 50, stimulation delivery module 52, impedance module 54, and telemetry module 58 are functionally integrated. In some examples, control module 50, stimulation delivery module 52, impedance module 54, and telemetry module 58 correspond to individual hardware units, such as ASICs, DSPs, FPGAs, or other hardware units.

Memory 56 stores stimulation programs 66 that specify stimulation parameter values for the electrical stimulation provided by IMD 16. In some examples, memory 56 also stores bladder data 69, which control module 50 may use for controlling the timing of the delivery of the electrical stimulation (e.g., beginning and termination of the sub-threshold electrical stimulation). For example, bladder data 69 may include threshold values or baseline values for at least one of bladder impedance, bladder pressure, sacral or pudendal afferent nerve signals, bladder contraction frequency, or external urinary sphincter EMG templates. As described in further detail below, the threshold values and baseline values may indicate a particular physiological state, such as a particular bladder contraction frequency level or a condition indicative of a voiding-related physiological condition (e.g., a patient state in which there is a relatively high likelihood of an involuntary voiding event) usable as a therapy trigger event.

Memory 56 may also store instructions for execution by control module 50, in addition to stimulation programs 66 and bladder data 69. Information related to sensed bladder contractions, bladder impedance and/or posture of patient 14 may be recorded for long-term storage and retrieval by a user, and/or used by control module 50 for adjustment of stimulation parameters (e.g., amplitude, pulse width, and pulse rate) or for use as a therapy trigger event. In some examples, memory 56 includes separate memories for storing instructions, electrical signal information, stimulation programs 66, and bladder data 69. In other examples, control module 50 select new stimulation parameters for a stimulation program 66 or new stimulation program from stimulation programs 66 to use in the delivery of the electrical stimulation based on patient input and/or monitored physiological states after termination of the electrical stimulation.

Generally, stimulation delivery module 52 generates and delivers electrical stimulation under the control of control module 50. As used herein, controlling the delivery of electrical stimulation may also include controlling the termination of such stimulation to elicit the post-stimulation, desired therapeutic effect from patient 14. In some examples, control module 50 controls stimulation delivery module 52 by accessing memory 56 to selectively access and load at least one of stimulation programs 66 to stimulation delivery module 52. For example, in operation, control module 50 may access memory 56 to load one of stimulation programs 66 to stimulation delivery module 52.

By way of example, control module 50 may access memory 56 to load one of stimulation programs 66 to stimulation delivery module 52 for delivering the electrical stimulation to patient 14. A clinician or patient 14 may select a particular one of stimulation programs 66 from a list using a programming device, such as programmer 24 or a clinician programmer. Control module 50 may receive the selection via telemetry module 58. Stimulation delivery module 52 delivers the electrical stimulation to patient 14 according to the selected program for an extended period of time, such as minutes, hours, days, weeks, or until patient 14 or a clinician manually stops or changes the program.

During the time of delivery with the program, the electrical stimulation may not be delivered the entire time. Instead, delivery with a program generally indicates that the program may control when stimulation is delivered as well as when stimulation is terminated or withheld from patient 14. In some examples, the respective stimulation programs 66 may define a schedule of first time periods ("on" periods) and second time periods ("off" periods), such that a stimulation signal is not continuously delivered to patient 14, but periodically delivered in accordance with predetermined parameters for the electrical stimulation. The second time periods without stimulation may include those periods that start with the termination of the electrical stimulation to induce a post-stimulation, desired therapeutic effect. In other examples, control module 50 may determine the timing with which IMD 16 delivers stimulation to patient 14 according to different programs based on sensor input or patient input.

Stimulation delivery module 52 delivers electrical stimulation according to stimulation parameters. In some examples, stimulation delivery module 52 delivers electrical stimulation in the form of electrical pulses. In such examples, relevant stimulation parameters may include a voltage amplitude, a current amplitude, a pulse rate, a pulse width, a duty cycle, or the combination of electrodes 29 that stimulation delivery module 52 uses to deliver the stimulation signal. In other examples, stimulation delivery module 52 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 29 stimulation delivery module 52 uses to deliver the stimulation signal.

In some examples, the stimulation parameters for the stimulation programs 66 may be selected to relax bladder 12, e.g., to reduce a frequency of contractions of bladder 12, after termination of the electrical stimulation. An example range of stimulation parameters for the electrical stimulation that are likely to be effective in treating bladder dysfunction, e.g., upon application to the spinal, sacral, pudendal, tibial, dorsal genital, inferior rectal, or perineal nerves, are as follows:

1. Frequency or pulse rate: between about 0.5 Hz and about 500 Hz, such as between about 1 Hz and about 250 Hz, between about 1 Hz and about 20 Hz, or about 10 Hz.

2. Amplitude: between about 0.1 volts and about 50 volts, such as between about 0.5 volts and about 20 volts, or between about 1 volt and about 10 volts. Alternatively, the amplitude may be between about 0.1 milliamps (mA) and about 50 mA, such as between about 0.5 mA and about 20 mA, or between about 1 mA and about 10 mA.

3. Pulse Width: between about 10 microseconds (µs) and about 5000 µs, such as between about 100 µs and about 1000 µs, or between about 100 µs and about 200 µs.

Although a variety of intensities may be effective in inducing a post-stimulation therapeutic effect, electrical stimulation with a reduced intensity may be desired and beneficial to patient 14 in some examples. This lower intensity may reduce physiological responses during delivery of the stimulation, reduce undesirable side effects, reduce the severity of adaptation to the stimulation, and reduce power consumption by IMD 16. A lower stimulation intensity may result from a lower amplitude, pulse width, and/or pulse rate.

In one example, the electrical stimulation may be delivered with particular stimulation parameters to elicit the desired post stimulation therapeutic effect. The stimulation may include a pulse frequency between approximately 0.1 Hz to 50 Hz, such as between approximately 1.0 Hz and 20 Hz. The stimulation may have a pulse width between approximately 50 and 500 microseconds, such as between approximately 100 and 200 microseconds. The electrical stimulation may also have an amplitude selected such that the stimulation is below the therapeutic intensity threshold causing no desired therapeutic effect during stimulation but inducing the desired therapeutic effect after termination of the stimulation. In other examples, the sub-threshold electrical stimulation may have an amplitude selected such that the sub-threshold electrical stimulation is below the physiological threshold stimulation intensity for the patient (e.g., the motor or sensory thresholds). For example, the voltage amplitude may be selected from a range between approximately 0.1 and 10 volts, such as less than approximately 5 volts. Accordingly, in another example, the current amplitude may be selected from a range between approximately 0.1 and 10 mA, or such as less than approximately 5 mA. Because lower stimulation intensities that still induce a desired post-stimulation therapeutic effect may be used, either the voltage or current amplitude may be at lower values that approach a zero value in some examples. Any electrical stimulation may be delivered with continuous pulses or signals or bursts of pulses.

Additionally, the stimulation parameters of stimulation programs 66 may include a duration of the first time period during which stimulation is delivered and a duration of the second time period during which stimulation is not delivered and the post-stimulation, desired therapy effect is delivered. In some examples, the duration of the first time period is at least five minutes, such as between about five minutes and about 30 minutes, between approximately 10 minutes and 20 minutes, or about 15 minutes. Hence, in some examples, stimulation delivery module 52 delivers electrical stimulation to patient 14 via electrodes 29 for a duration of at least five minutes, such as between about five minutes and about 30 minutes, between approximately 10 minutes and 20 minutes, or about 15 minutes.

In some examples the duration of the second period, during which stimulation delivery module 52 does not deliver the electrical stimulation to patient 14, is at least five minutes, such as between five minutes and about 30 minutes or between about 10 minutes and about 20 minutes. In other examples, the second period may be longer to accommodate prolonged therapeutic effects after the termination of the electrical stimulation.

In addition, a lockout period may encompass at least a portion of the second period. The lockout period may prevent stimulation delivery module 52 from delivering any stimulation to patient 14 during the lockout period. In this manner, the lockout period may prevent patient 14 from requesting another round (e.g., another first period of time) of electrical stimulation that may interfere with the induced post-stimulation therapeutic effect of the second period. Generally, the lockout period may begin immediately upon the termination of the electrical stimulation. The lockout period may be adjusted by a user, e.g., a clinician or technician, or IMD 16 to match various durations of the induced post-stimulation therapeutic effect.

In some examples, the stimulation parameter values are selected from among those listed above such that the electrical stimulation induces a physiological response related to voiding of patient 14 during the second time period after termination of the electrical stimulation, i.e., the post-stimulation therapeutic effect. In some examples, the stimulation parameters are selected such that the electrical stimulation causes substantially no inhibitory physiological response related to voiding of patient 14 during the first time period, or an inhibitory physiological response that is less than the desired physiological response associated with the post-stimulation therapeutic effect. Again, an example of an inhibitory physiological response may be a reduction in bladder contraction frequency after termination of the electrical stimulation. In some examples, the physiological response of patient 14 may be substantially similar during the first time period and during a time period prior to the first time period during which stimulation delivery module 52 delivers electrical stimulation to patient 14.

In some examples, at least some of stimulation programs 66 may define a stimulation intensity that is less than a physiological threshold stimulation intensity, e.g., a sub-threshold stimulation ineffective to produce an acute physiological response. The physiological threshold stimulation intensity may be defined as the stimulation intensity at which an physiological response of patient 14 is first observed when increasing the stimulation intensity from a relatively low intensity to a higher intensity, e.g., by manipulation of one or more parameters than contribute to intensity, such as amplitude, pulse rate, or pulse width. Stated another way, the physiological threshold stimulation intensity may be defined as approximately the lowest stimulation intensity that causes an acute, physiological significant, response of patient 14. In some examples, an acute response may be defined as a physiological response that occurs within about 30 seconds of patient 14 receiving the stimulation. In some examples, whether a response is physiologically significant may be defined by patient 14. As described above, the acute response may be a motor response, perceived response, or detected physiological response. In one example, the stimulation may cause a motor response in the form of movement of a toe of patient 14, and patient 14 may define the movement of the toe as physiologically significant when the movement of the toe is perceptible or when the movement of the toe is above some arbitrary amount defined by patient 14.

In some implementations, control module 50 may determine the physiological threshold stimulation intensity by setting stimulation parameters (e.g., a current amplitude, a voltage amplitude, a frequency or pulse rate, a pulse width, a shape, a duty cycle, and/or the combination of electrodes 29) to produce a relatively low stimulation intensity and controlling stimulation delivery module 52 to deliver stimulation to patient 14 via electrodes 29 using these stimulation parameter values. If no acute physiological response is detected during the stimulation, control module 50 may change one or more stimulation parameters automatically or in response to an input received from a user via programmer 24 and telemetry module 58, while the remaining parameters are kept approximately constant, and control module 50 may again control stimulation delivery module 52 to deliver stimulation at the new stimulation intensity. This may be repeated until an acute physiological response is detected or observed. Although only one parameter may be adjusted to achieve the threshold stimulation intensity, other parameters may be adjusted as well in other examples. When stimulating one of the nerves described herein, such as a spinal nerve, sacral nerve, pudendal nerve, or the like, the observed or detected physiological response may be a contraction of a toe of patient 14, a flexing of an anal sphincter of patient 14, or a detected signal on an electromyogram (EMG). The physiological response may be observed by patient 14 or a clinician or may be detected by sensor 22 or electrodes 19, 21 coupled to IMD 16. Other physiological responses may be detected when stimulating other nerves of patient 14.

In some examples, once the physiological threshold stimulation intensity for producing an acute physiological response from patient 14 is determined, control module 50 may define a stimulation program, automatically or in response to an input received from a clinician via programmer 24 and telemetry module 58. The stimulation program may be stored as one of stimulation programs 66 in memory 56. In some examples, the stimulation program may include stimulation parameters that define a stimulation intensity that is between about 50% and about 100% of the physiological threshold stimulation intensity. In other examples, the stimulation program may include stimulation parameters that define a stimulation intensity that is less than or equal to about 50% of the physiological threshold stimulation intensity. In some implementations, the stimulation program may include stimulation parameters that define a stimulation intensity that is less than or equal to about 75% of the physiological threshold intensity.

In each case, the stimulation intensity is selected to be sufficient to cause the desired therapeutic effect after stimulation is terminated, but, in some examples, not during delivery of stimulation to patient 14. For example, the stimulation may be selected to have an amplitude that is less than or equal to about 50%, or less than or equal to about 75% of an amplitude necessary to meet the physiological threshold, while pulse rate or pulse width are the same. In addition, or alternatively, the intensity may be selected based on percentages of pulse width, or pulse rate, or a combination of pulse width, pulse rate, and/or amplitude relative to the corresponding values associated with the physiological threshold. However, in some examples, stimulation intensity may be adjusted by adjusting amplitude only while keeping pulse rate and/or pulse width in a range observed to be effective in supporting the therapeutic effect.

In examples of electrical stimulation configured to induce a desired therapeutic response after stimulation, but no desired therapeutic response during stimulation, a similar method may be used to determine the stimulation intensity delivered to patient 14 based on the therapeutic intensity threshold. As described above, the therapeutic intensity threshold may be used to determine the intensity at which an acute therapeutic response is observed in patient 14. Then, the stimulation intensity may be set to some lower intensity that still induces the desired therapeutic effect after termination of the stimulation. In this manner, the stimulation program may include stimulation parameters that define a stimulation intensity that is between about 50% and about 100% of the therapeutic intensity threshold. In other examples, the stimulation program may include stimulation parameters that define a stimulation intensity that is less than 50% of the therapeutic intensity threshold. In some implementations, the stimulation program may include stimulation parameters that define a stimulation intensity that is about 75% of the therapeutic intensity threshold. Hence, the therapeutic threshold or physiological threshold may be determined, and then a lower intensity stimulation level may be selected as a percentage of a selected one of the thresholds, e.g., based on a percentage of the amplitude associated with the selected threshold, or one or more of amplitude, pulse width or pulse rate. As mentioned above, in some examples, the electrical stimulation parameter values are selected based on the selected threshold such that the stimulation induces a desired therapeutic effect in patient 14 after the electrical stimulation is terminated (e.g., when no stimulation is being delivered to patient 14) and not during stimulation. In other examples, the electrical stimulation may be an electrical stimulation below the therapeutic threshold that does not provide, or is insufficient to cause, an acute physiological response in the patient during the delivery of the stimulation. However, the sub-threshold electrical stimulation may still be sufficient to cause the desired therapeutic effect after stimulation is terminated.

Rather than setting the intensity level based on a percentage of the therapeutic intensity threshold or the physiological intensity threshold, as described above, in some examples, a clinician may seek an intensity level based on a maximum level at which the stimulation does not produce the desired therapeutic effect during stimulation and a minimum level for which the stimulation causes the desired therapeutic effect after stimulation is terminated. In some examples, the maximum intensity level may be determined experimentally by increasing the intensity level during stimulation until the desired therapeutic effect is perceived. In addition, in some examples, the minimum intensity may then be determined through one or more iterations of lowering the intensity level from the maximum level until the desired therapeutic effect no longer occurs after termination of the stimulation. In other words, the minimum level may the lowest intensity level at which the desired therapeutic effect still occurs after stimulation is terminated. In other cases, a clinician may find it desirable to select a stimulation level sufficient to provide no more than an ancillary therapeutic effect during stimulation while also producing the greater desired therapeutic effect after stimulation.

The stimulation intensity may be changed from the therapeutic intensity threshold by adjusting a value of at least one of the stimulation parameters described above, such as, for example, a current amplitude, a voltage amplitude, a frequency or pulse rate, a pulse width, a burst duty cycle, a pulse duty cycle, a signal shape, a signal duty cycle, or the combination and polarities of electrodes 29. For example, the current or voltage amplitude of the stimulation signal may be reduced to reduce an intensity of the stimulation signal.

In some examples, at least some of stimulation programs 66 may define values for a set of stimulation parameters, including the durations of the first and second time periods, which cause stimulation delivery module 52 to deliver stimulation therapy to patient 14 in an open loop manner. In such cases, stimulation delivery module 52 delivers stimulation to patient 14 during each of the first time periods according to the same stimulation parameters. Additionally, the first and second time periods alternate and each first time period has the same duration and each second time period has the same duration. However, the first periods may be the same as or different than the second periods. In some examples, stimulation delivery module 52 continues to deliver stimulation therapy to patient 14 according to these stimulation parameters until receiving an instruction from control module 50 to interrupt therapy delivery. In some examples, control module 50 may issue such an instruction to stimulation delivery module 52 in response to receiving an input for a user, such as a clinician, via telemetry module 58.

At least one of stimulation programs 66 may define stimulation parameters that cause stimulation delivery module 52 to deliver electrical stimulation to patient 14 in a closed loop manner. In closed loop stimulation therapy, control module 50 or stimulation delivery module 52 may deliver stimulation therapy to patient based on at least one feedback, e.g., a signal representative of a detected physiological state of patient 14 sensed by at least one of sensor 22, electrode 19, or electrode 21. This physiological state may be a therapy trigger event used to terminate the electrical stimulation, thereby eliciting the desired therapeutic effect from patient 14. For example, control module 50 or stimulation delivery module 52 may control delivery of electrical stimulation by stimulation delivery module 52 based on a contraction frequency of bladder 12. In some examples, the control of electrical stimulation delivery by control module 50 or stimulation delivery module 52 may include controlling a duration of the second time period during which stimulation delivery module 52 does not deliver stimulation therapy to patient 14.

To facilitate delivery of stimulation in a closed loop manner, the at least one of stimulation programs 66 may include a baseline contraction frequency or a threshold contraction frequency. The baseline contraction frequency may be contraction frequency of bladder 12 at a time prior to delivery of the electrical stimulation by stimulation delivery module 52. For example, the baseline contraction frequency of bladder 12 may be sensed and determined by control module 50 after implantation of IMD 16 in patient 14, but before stimulation delivery module 52 delivers any electrical stimulation to patient 14. In some examples, the baseline contraction frequency of bladder 12 may represent the patient state when no therapeutic effects from delivery of stimulation by IMD 16 are present.

Control module 50 may determine the baseline contraction frequency of bladder 12 using any suitable technique. In one example, control module 50 determines the baseline contraction frequency by utilizing signals representative of physiological parameters received from at least one of sensor 22, electrodes 19 or electrodes 21. In some examples, control module 50 monitors impedance of bladder 12 to detect contraction of bladder 12 based on signals received from impedance module 54. For example, control module 50 may determine an impedance value based on signals received from impedance module 54 and compare the determined impedance value to a threshold impedance value stored in memory 56 as bladder data 69. When the determined impedance value is less than the threshold value stored in bladder data 69, control module 50 detects bladder contraction. In some implementations, control module 50 monitors impedance of bladder 12 for a predetermined duration of time to detect contractions of bladder 12, and determines the baseline contraction frequency of bladder 12 by determining a number of contractions of bladder 12 in the predetermined duration of time. In other examples, electrodes 19 or 21 may be used to detect an EMG of the detrusor muscle to identify bladder contraction frequencies. Alternatively, a strain gauge sensor signal output or other measure of bladder contraction change may be used to detect the physiological state of bladder 12.

In an example closed loop configuration, control module 50 may begin the electrical stimulation upon the detection of a moderate bladder contraction frequency, which can be defined by, for example, a threshold bladder contraction frequency stored by memory 56 or another device (e.g., programmer 24). This physiological state of bladder 12 may indicate that a therapeutic effect should be delivered during an impending second time period, e.g. therapy window. Once control module 50 detects a heightened frequency of bladder 12 contractions, e.g., a full bladder physiological state, control module 50 may terminate the electrical stimulation to induce the post-stimulation therapeutic effect of reducing contractions of bladder 12.

In the example illustrated in FIG. 2, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, control module 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Control module 50 determines an impedance value from the measure voltage values received from voltage measurement circuitry 52.

In other examples, control module 50 may monitor signals received from sensor 22 to detect contraction of bladder 12 and determine the baseline contraction frequency. In some examples, sensor 22 may be a pressure sensor for detecting changes in pressure of bladder 12, which control module 50 may correlate to contractions of bladder 12. Control module 50 may determine a pressure value based on signals received from sensor 22 and compare the determined pressure value to a threshold value stored in bladder data 69 to determine whether the signal is indicative of a contraction of bladder 12. In some implementations, control module 50 monitors pressure of bladder 12 to detect contractions of bladder 12 for a predetermined duration of time, and determines a contraction frequency of bladder 12 by calculating a number of contractions of bladder 12 in the predetermined time period.

In some examples, control module 50 may cause a threshold contraction frequency to be stored as bladder data 69 in memory 56, and may utilize the threshold contraction frequency to deliver electrical stimulation in a closed loop manner, e.g., to determine when to begin and terminate delivery of the electrical stimulation to patient 14 according to a particular stimulation program. In some implementations, control module 50 may, automatically or under control of a user, determine the threshold contraction frequency based on a baseline contraction frequency. For example, control module 50 may determine the threshold contraction frequency as a predetermined percentage of the baseline contraction frequency or a percentage of the baseline contraction frequency input by a user via programmer 24. As one example, the threshold frequency may be between approximately 75% and approximately 100% of the baseline contraction frequency.

In some examples, the threshold contraction frequency may not be based on a baseline contraction frequency of patient 14, and may instead be based on clinical data collected from a plurality of patients. For example, the threshold contraction frequency may be determined based on an average bladder contraction frequency of a plurality of patients during a bladder filling time period, i.e., during a time period in which the plurality of patients are not experiencing a voluntary or involuntary voiding event. In any case, the threshold contraction frequency may be stored in bladder data 69, and, in some examples, control module 50 may utilize the threshold contraction frequency for comparison to detected bladder contractions when delivering stimulation therapy in a closed loop manner to patient 14. In this manner, the detected bladder contractions may be used as a therapy trigger event based on the threshold contraction frequency.

When the detected bladder contractions exceed the threshold contraction frequency, control module 50 may terminate electrical stimulation to produce the desired therapeutic effect after termination, or start electrical stimulation is not already started, and then terminate the electrical stimulation after a sufficient period of time to produce the desired therapeutic effect after termination. Control module 50 may repetitively continue to cycle through application of electrical stimulation for a first period of time and then terminate the stimulation to cause the post-stimulation, desired therapeutic effect during a second period of time immediately following the first period of time, while the detected threshold contraction frequency continues to exceed the threshold contraction frequency. Control module 50 may delay delivery of electrical stimulation or termination of electrical stimulation when it is determined that the detected contraction frequency does not exceed the threshold contraction frequency.

In other examples, instead of utilizing a threshold contraction frequency or a baseline contraction frequency from other patients, control module 50 may control closed-loop delivery of stimulation therapy based on EMG signals of patient 14. In some implementations, sensor 22 may include an EMG sensor, and control module 50 may generate an EMG from the received signals generated by sensor 22. Sensor 22 may be implanted proximate to a muscle which is active when bladder 12 is contracting, such as a detrusor muscle. Control module 50 may compare an EMG collected during the second time period to EMG templates stored as bladder data 69 (e.g., a short-term running average) to determine whether the contractions of bladder 12 are indicative of a predetermined characteristic which causes control module 50 to control therapy delivery module 52 to terminate delivery of the stimulation therapy. For example, the predetermined characteristic may be a frequency of contractions of bladder, an amplitude of the signal (representative of intensity of contractions of bladder 12), or the like. In some examples, control module 50 can determined, based on the EMG signal generated by sensor 22, whether the frequency of bladder contractions indicate a return to a baseline contraction frequency or deviation from the baseline, such that termination of the stimulation delivery is desirable. In some cases, control module 50 may generate the EMG template based on received signals generated by sensor 22 after implantation of IMD 16, but before stimulation delivery module 52 delivers any sub-threshold electrical stimulation to patient 14.

Control module 52 may utilize at least one of a threshold contraction frequency, a baseline contraction frequency, or detected EMG signals to control stimulation delivery module 52 to deliver stimulation therapy in a closed loop manner. For example, during at least the second time periods, control module 50 may monitor impedance of bladder 12 to detect contraction of bladder 12 based on signals received from impedance module 54. In some implementations, control module 50 substantially continuously monitors impedance of bladder 12, at least during the second time periods, to detect contraction of bladder 12, and determines a contraction frequency of bladder 12 by determining a number of contractions of bladder 12 in a specified time period.

In other examples, sensor 22 may be a pressure sensor and control module 50 may monitor signals received from sensor 22 during at least a portion of the second time period to detect contraction of bladder 12. In some implementations, control module 50 substantially continuously monitors pressure of bladder 12, at least during the second time periods, to detect contraction of bladder 12, and determines a contraction frequency of bladder 12 by determining a number of contractions of bladder 12 in a specified time period.

After determining a contraction frequency of bladder 12, control module 50 may compare the determined contraction frequency of bladder 12 to the threshold contraction frequency stored in memory 56 as bladder data 69. When the determined contraction frequency is greater than or substantially equal to the threshold contraction frequency stored in bladder data 69, control module 50 may control stimulation delivery module 52 to initiate delivery of electrical stimulation to patient 14 (e.g., to begin the first period of time). However, if the delivery of electrical stimulation has already begun, control module 50 may terminate the electrical stimulation once the determined contraction frequency is greater than or substantially equal to the threshold contraction frequency stored in bladder data 69.

In other examples, control module 50 may compare the determined contraction frequency of bladder 12 and the baseline contraction frequency to determine a difference between the determined contraction frequency and the baseline contraction frequency. In some examples, when the difference is less than or equal to a specified value (e.g., a threshold difference value) control module 50 may cause stimulation delivery module 52 to initiate delivery of electrical stimulation to patient 14 or terminate electrical stimulation to immediately induce a desired therapeutic effect.

In other examples, sensor 22 may include an EMG sensor, and processor 50 may generate an EMG from the received signals generated by sensor 22 (e.g., which may sense the muscle activity with one or more sensor positioned near the target muscle) and compare the EMG to an EMG template stored as bladder data 69 to determine whether the contractions of bladder 12 are indicative of a predetermined characteristic which causes control module 50 to control stimulation delivery module 52 to initiate delivery of the electrical stimulation. For example, the predetermined characteristic may be a frequency of contractions of bladder, an amplitude of the signal (representative of intensity of contractions of bladder 12), or the like.

In some implementations, closed loop therapy may allow control module 50 and stimulation delivery module 52 to deliver more efficacious therapy to patient 14 by timing the delivery of the electrical stimulation to respond to or anticipate a specific physiological state (e.g., a bladder contraction frequency level) of patient 14. For example, based on the determined contraction frequency of bladder 12, control module 50 may cause stimulation delivery module 52 to initiate delivery of electrical stimulation to patient 14 in advance of the therapy window needed to provide a therapeutic effect to patient 14.

As discussed above, delivery of electrical stimulation during the first time period may generate a desired therapeutic effect (e.g., a physiological response that alleviates a previous condition) that helps prevent the occurrence of an involuntary voiding event, whereby the therapeutic effect occurs only after termination of the electrical stimulation. Thus, by timing the delivery of the electrical stimulation to occur prior to observing a return to increased bladder contraction frequencies (e.g., at or above the threshold), control module 50 may help time therapy such that there is sufficient time for the electrical stimulation to generate the desired therapeutic effect. In some examples, the first time period during which the electrical stimulation is delivered to patient 14 is selected to generate the desired post-stimulation therapeutic effect (e.g., a particular percentage reduction in bladder contraction frequency or a particular bladder contraction frequency value) during the second time period. The delivery of the electrical stimulation by therapy module 52 does not generate an acute physiological response in patient 14 prior to the termination of the electrical stimulation. In particular, the electrical stimulation has an intensity insufficient to generate the desired post-stimulation therapeutic effect during the stimulation.

In the example of FIG. 2, stimulation delivery module 52 drives electrodes on a single lead 28. Specifically, stimulation delivery module 52 delivers sub-threshold electrical stimulation to tissue of patient 14 via selected electrodes 29A-29D carried by lead 28. A proximal end of lead 28 extends from the housing of IMD 16 and a distal end of lead 28 extends to a target therapy site, such as a spinal nerve (e.g., an S3 nerve), or a therapy site within the pelvic floor, such as tissue sites proximate a sacral nerve, a pudendal nerve, a tibial nerve, a dorsal genital nerve, an inferior rectal nerve, a perineal nerve, a hypogastric nerve, a urinary sphincter, or any combination thereof. In other examples, stimulation delivery module 52 may deliver electrical stimulation with electrodes on more than one lead and each of the leads may carry one or more electrodes. The leads may be configured as an axial leads with ring electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

As previously described, sensor 22 may comprise a pressure sensor configured to detect changes in bladder pressure, electrodes for sensing pudendal or sacral afferent nerve signals, or electrodes for sensing external urinary sphincter EMG signals (or anal sphincter signals in examples in which IMD 16 provides fecal urgency or fecal incontinence therapy), or any combination thereof. Additionally or alternatively, sensor 22 may comprise a motion sensor, such as a two-axis accelerometer, three-axis accelerometer, one or more gyroscopes, pressure transducers, piezoelectric crystals, or other sensors that generate a signal that changes as patient activity level or posture state changes. Control module 50 may detect a patient condition indicative of a high probability of an incontinence event (e.g., a particular bladder contraction frequency level or abnormal detrusor muscle activity) or other trigger events based on signals received from sensor 22 in addition to instead of impedance module 54. Sensor 22 may also be a motion sensor that is responsive to tapping (e.g., by patient 14) on skin superior to IMD 16 and, as previously described, control module 50 may control therapy module 52 to deliver the electrical stimulation or terminate the electrical stimulation in response to detection of the patient tapping.

In examples in which sensor 22 includes a motion sensor, control module 50 may determine a patient activity level or posture state based on a signal generated by sensor 22. This patient activity level may be, for example, sitting, exercising, working, running, walking, or any other activity of patient 14. For example, control module 50 may determine a patient activity level by sampling the signal from sensor 22 and determining a number of activity counts during a sample period, where a plurality of activity levels are associated with respective activity counts. In one example, control module 50 compares the signal generated by sensor 22 to one or more amplitude thresholds stored within memory 56, and identifies each threshold crossing as an activity count. In any of these cases in which control module 50 controls the sub-threshold electrical stimulation in closed-loop fashion, the data used to terminate the stimulation may be considered therapy trigger events.

In some examples, control module 50 may control stimulation delivery module 52 to deliver or terminate the electrical stimulation based on patient input received via telemetry module 58. Telemetry module 58 includes any suitable hardware, firmware, software or any combination thereof for communicating with another device, such as programmer 24 (FIG. 1). Under the control of control module 50, telemetry module 58 may receive downlink telemetry, e.g., patient input, from and send uplink telemetry, e.g., an alert, to programmer 24 with the aid of an antenna, which may be internal and/or external. Control module 50 may provide the data to be unlinked to programmer 24 and the control signals for the telemetry circuit within telemetry module 58, and receive data from telemetry module 58.

Generally, control module 50 controls telemetry module 58 to exchange information with medical device programmer 24 and/or another device external to IMD 16. Control module 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 3:
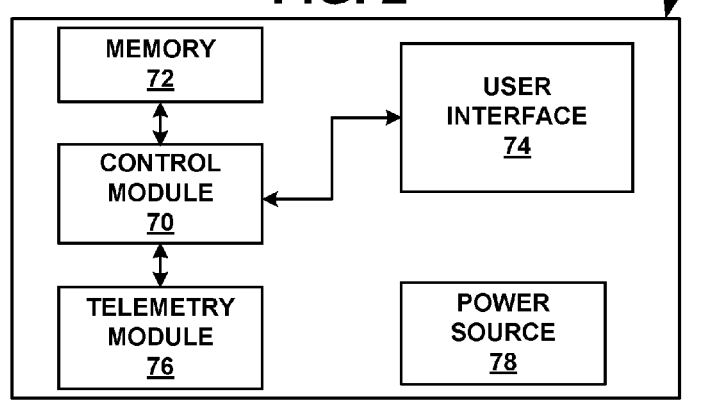
FIG. 3 is a block diagram illustrating an example configuration of an external programmer which may be utilized in the system of FIG. 1.

FIG. 3 is a block diagram illustrating an example configuration of an external programmer 24. While programmer 24 may generally be described as a hand-held computing device, the programmer may be a notebook computer, a cell phone, or a workstation, for example. As illustrated in FIG. 3, external programmer 24 may include a control module 70, memory 72, user interface 74, telemetry module 76, and power source 78. Memory 72 may store program instructions that, when executed by control module 70, cause control module 70 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and control module 70, user interface 74, and telemetry module 76 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 72, such as RAM, ROM, PROM, EPROM, EEPROM, flash memory, a hard disk, a CD-ROM, comprising executable instructions for causing the one or more processors to perform the actions attributed to them. Moreover, although control module 70 and telemetry module 76 are described as separate modules, in some examples, control module 70 and telemetry module 76 are functionally integrated. In some examples, control module 70 and telemetry module 76 and telemetry module 58 correspond to individual hardware units, such as ASICs, DSPs, FPGAs, or other hardware units.

Memory 72 may store program instructions that, when executed by control module 70, cause control module 70 and programmer 24 to provide the functionality ascribed to programmer 24 throughout this disclosure. In some examples, memory 72 may further include program information, e.g., stimulation programs defining the electrical stimulation, similar to those stored in memory 56 of IMD 16. The stimulation programs stored in memory 72 may be downloaded into memory 56 of IMD 16.

User interface 74 may include a button or keypad, lights, a speaker for voice commands, a display, such as a liquid crystal (LCD), light-emitting diode (LED), or cathode ray tube (CRT). In some examples the display may be a touch screen. As discussed in this disclosure, control module 70 may present and receive information relating to electrical stimulation and resulting therapeutic effects via user interface 74. For example, control module 70 may receive patient input via user interface 74. The input may be, for example, in the form of pressing a button on a keypad or selecting an icon from a touch screen.

Control module 70 may also present information to the patient in the form of alerts related to delivery of the electrical stimulation to patient 14 or a caregiver, as described in more detail below, via user interface 74. Although not shown, programmer 24 may additionally or alternatively include a data or network interface to another computing device, to facilitate communication with the other device, and presentation of information relating to the electrical stimulation and therapeutic effects after termination of the electrical stimulation via the other device.

Telemetry module 76 supports wireless communication between IMD 16 and programmer 24 under the control of control module 70. Telemetry module 76 may also be configured to communicate with another computing device via wireless communication techniques, or direct communication through a wired connection. In some examples, telemetry module 76 may be substantially similar to telemetry module 58 of IMD 16 described above, providing wireless communication via an RF or proximal inductive medium. In some examples, telemetry module 76 may include an antenna, which may take on a variety of forms, such as an internal or external antenna.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 16 and/or programmer 24 may control of the timing of the delivery of the sub-threshold electrical stimulation that generates a physiological response (e.g., a therapeutic response) from patient 14 upon termination of the electrical stimulation to manage bladder dysfunction, for example. If external programmer 24 controls the stimulation, programmer 24 may transmit stimulation programs for implementation by control module 50 to IMD 16 via telemetry module 76. A user (e.g., patient 14 or a clinician) may select the time at which the therapy window begins (e.g., the beginning of the second time period), the duration of the therapy window (e.g., the duration of the second time period after the termination of the electrical stimulation), and/or the beginning time for the electrical stimulation via a display of user interface 74. In other examples, the user may select a specific stimulation program or rate the effectiveness of a particular stimulation program from a list presented via a display of user interface 74. Programmer 24 can also be configured to transmit a signal to IMD 16 indicating that control module 50 should execute locally stored programs or therapy routines. In such a manner, control over the electrical stimulation may be distributed between IMD 16 and external programmer 24, or may reside in either one alone.

In some examples, patient 14 may provide an input that requests a therapy, e.g., the therapeutic effects induced after electrical stimulation termination, via programmer 24. This patient input may be a therapy trigger event upon which IMD 16 terminates the electrical stimulation. In this way, patient 14 may use programmer 24 to control when the therapeutic effect is induced (e.g., the beginning of the therapy window) by initiating the termination of the electrical stimulation. Patient 14 may also use programmer 24 to begin the electrical stimulation when therapy is desired, but the therapeutic effect would be delayed until the electrical stimulation can be terminated, i.e., following the first period of time. Both of these examples may be considered "on demand" therapy, but starting the electrical stimulation would be more of a "delayed on demand" than merely requesting termination of stimulation.

In other examples, patient 14, or any other user, may utilize programmer 24 to create various schedules, times of the day, or activities in which patient 14 would like to target the therapy window. The therapy window may start soon after (e.g., within about 2 minutes to about 10 minutes) the termination of the electrical stimulation. In one example, the therapy window may start within approximately 2 minutes to 5 minutes of the termination of the electrical stimulation. For example, if patient 14 typically would desire a therapeutic effect that quiets bladder contractions during a car drive home from work, patient 14 use programmer 24 to schedule the electrical stimulation to start ahead of the desired therapy window. If the therapy window is selected to be between 5:30 P.M and 6:00 P.M. and the electrical stimulation must be delivered for 15 minutes prior to termination, programmer 24 may control IMD 16 to begin the delivery of the electrical stimulation at 5:15 P.M and terminate the stimulation at 5:30 P.M. In this manner, programmer 24 may be used to provide some automation to the therapy and update parameters that define when the electrical stimulation is started and terminated.

Power source 78 delivers operating power to the components of programmer 24. Power source 78 may include a battery and a power generation circuit to produce the operating power. In some examples, the battery may be rechargeable to allow extended operation.

Figure 4:
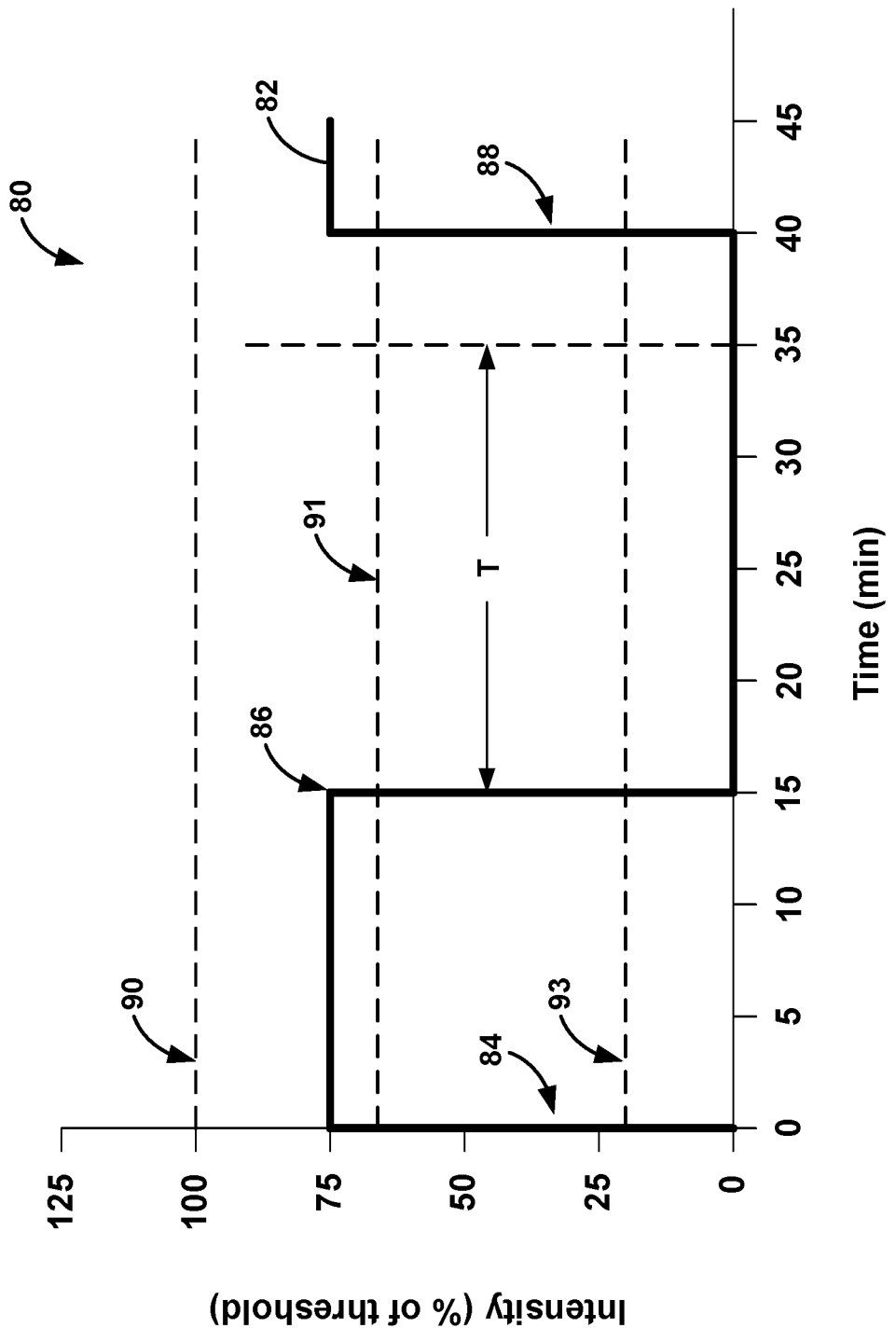
FIG. 4 is an example timing diagram of sub-threshold electrical stimulation delivered to induce a therapeutic effect after stimulation termination.

FIG. 4 is an example timing diagram 80 of electrical stimulation delivered to induce a post-stimulation therapeutic effect after stimulation termination. As shown in FIG. 4, timing diagram 80 includes stimulation cycle 82. Stimulation cycle 82 is a representation of an example duty cycle for electrical stimulation delivered to patient 14 to induce a desired therapeutic effect after termination of the electrical stimulation. Timing diagram 80 illustrates the intensity of the electrical stimulation during stimulation cycle 82, as a percentage of therapeutic threshold 90, over time in minutes. Therapeutic threshold 90 may be the therapeutic intensity threshold previously identified for patient 14, e.g., the intensity at which the desired therapeutic effect is produced during stimulation. The intensity may be at least partially defined by either a current or voltage amplitude. In some examples, the intensity may also be defined by a pulse width, pulse frequency, and/or burst frequency.

Hence, the stimulation intensity may be conveniently selected in a relatively simple manner based on a percentage of the therapeutic (or physiological) threshold for generation of a desired therapeutic effect. For example, a percentage of an amplitude associated with the threshold may be selected, or percentages of one or more of amplitude, pulse width or pulse rate may be selected. Some range of percentages may be found to be effective in providing electrical stimulation that causes the desired therapeutic effect post-stimulation, but does not cause the desired therapeutic effect during stimulation. The range of percentages can be determined based on experimentation on patient 14 or based on experimentation on a group of patients.

In other examples, the intensity of the electrical stimulation may be selected more precisely based on experimentation to determine other thresholds related to generation of the desired therapeutic effect after stimulation is terminated. In particular, the intensity of the electrical stimulation may be determined to be not only less than the therapeutic intensity threshold 90 sufficient to generate the desired therapeutic effect during stimulation, but also below a physiological threshold stimulation intensity, shown as threshold 91, sufficient to produce the an acute physiological response (e.g., a motor response) during the stimulation. However, in other examples, the intensity of the stimulation may also be selected to be above threshold 91, as shown in FIG. 4.

In order to induce the desired therapeutic effect after termination of stimulation, the intensity may need to remain above a minimum threshold 93. Thresholds 90, 91, and 93 are shown merely for purposes of illustration of the threshold concepts for selection of stimulation intensity of stimulation cycle 82 and are not intended to indicate any actual thresholds for any particular patient or patient population. Rather, one or more of such thresholds may be determined for individual patients and used to set appropriate stimulation intensity levels by manipulation of one or more stimulation parameters.

Stimulation cycle 82 begins at time zero with stimulation delivery event 84. Stimulation delivery event 84 may be any detected event that calls for the initiation, or the beginning, of electrical stimulation. In some cases, if electrical stimulation is not already being applied, stimulation delivery event 84 may be a therapy trigger event. In addition, or instead, stimulation delivery event 84 may be the start of a timer, the expiration of a previous time period, a detected physiological state, or a patient input from programmer 24. In the example shown in FIG. 4, the intensity of stimulation cycle 82 is changed from zero to approximately 75% of threshold 90 (or threshold 91), e.g., by adjusting stimulation amplitude to be about 75% of the stimulation amplitude associated with threshold 90, or adjusting another parameter such as pulse width or pulse rate in a similar manner. In other examples, stimulation cycle 82 may include other intensities. The change in intensity may occur immediately or ramp up over a predetermined ramp period or at a predetermined ramp rate (e.g., via a step-wise ramp function, a linear ramp function, or a non-linear ramp function). Ramping up to the desired intensity of the electrical stimulation may prevent or reduce perception by patient 14. Although the stimulation intensity may include amplitudes well above zero, the amplitude may be lowered, for example, when the electrode is positioned closer to a nerve. In this case, the amplitude may even approach zero in order to deliver an intensity that is sufficient to induce a desired post-stimulation therapeutic effect.

In the example shown in FIG. 4, the electrical stimulation (e.g., the "ON" portion of stimulation cycle 82) may be delivered at an intensity below therapeutic threshold 90. This electrical stimulation may be, for example, between 50% and 100% of therapeutic threshold 90, e.g., 75% in the example of FIG. 4. In some examples, the electrical stimulation may be delivered at an intensity below 50% of therapeutic threshold 90. Alternatively, the electrical stimulation may be selected based on a percentage of physiological threshold 91. The lowest intensity threshold 93 of stimulation that is still sufficient to induce a post-stimulation therapeutic effect may be different for each patient and may need to be experimentally determined, as discussed above. In other examples, electrical stimulation of stimulation cycle 82 may be provided with an intensity above physiological threshold 91. Although this above threshold stimulation may cause some type of acute physiological response in patient 14, the response may generally be minimal when compared to the desired therapeutic effect induced after termination of the electrical stimulation (e.g., an ancillary therapeutic effect less than 20% of the post-stimulation therapeutic effect). Because the desired therapeutic effect is an induced effect after termination of the electrical stimulation, e.g., during the "OFF" phase of stimulation cycle 82, the exact intensity for the electrical stimulation may vary from patient to patient.

When IMD 16 delivers stimulation to patient 14 according to stimulation cycle 82, stimulation is delivered to patient 14 for approximately 15 minutes before termination. This 15 minute period between minutes zero and 15, or between stimulation delivery event 84 and therapy trigger event 86, represents the first time period. In some examples, the duration of the first time period may generally be between five minutes and 30 minutes, or between approximately 10 minutes and 20 minutes. The first time period may be selected and customized for a specific patient 14, in some examples.

When the intensity of stimulation cycle 82 is non-zero, the electrical stimulation being delivered is may not be a continuous pulse of electrical stimulation. Instead, in some examples, in a stimulation interval extending from the start of electrical stimulation delivery at stimulation delivery event 84 to the termination of stimulation at therapy trigger event 86, the sub-threshold electrical stimulation may include multiple pulses delivered at a given pulse rate and pulse width. For example, IMD 16 may deliver a continuous train or pulses or bursts of pulses during the electrical stimulation between minutes 0 and 15 in FIG. 4, i.e., in the stimulation interval between events 84 and 86. The intensity shown by stimulation cycle 82 may be a peak intensity of each of the pulses delivered during the stimulation interval or an average of each pulse peak intensity in the stimulation interval if not all pulses are equal.

After IMD 16 detects therapy trigger event 86, IMD 16 terminates the delivery of the electrical stimulation such that the stimulation interval ends and stimulation cycle 82 returns to zero intensity. As described above, therapy trigger event 86 may be generated in response to an elapsed time period (e.g., the end of the first time period), a detected physiological state of patient 14 (e.g., an above threshold bladder contraction frequency or bladder pressure), a user input (e.g., a patient request for a therapeutic effect), or any other event that would indicate the termination of the electrical stimulation.

Therapy window T may be the desired time period during which the post-stimulation, desired therapeutic effect is to occur, such as a post-stimulation inhibitory effect on bladder contraction. For example, therapy window T may be a normal time during which patient 14 may benefit from quieting of bladder contractions, i.e., reduction in bladder contraction frequency. Stimulation cycle 82 may be defined by a stimulation program such that the termination of the electrical stimulation is equal to, or occurs prior to, the start of therapy window T. Although therapy window T may be a time period, in other examples, therapy window T may simply be defined by the start of therapy window T. As shown in FIG. 4, in one example, therapy window T may be approximately 20 minutes in duration.

During therapy window T, IMD 16 may be locked out from delivering subsequent electrical stimulation. This lockout period may be provided so that the therapeutic effect has time to be induced and any other stimulation does not interfere with the therapeutic effect. In other words, electrical stimulation delivered during therapy window T may prevent the therapeutic effect from being induced. The lockout period may coincide with the time period of desired therapy window T or the second time period between successive sub-threshold stimulation delivery events 86 and 88. However, the lockout period may be shorter or longer than the therapy window in other examples. The lockout period may be initiated upon detection of therapy trigger event 86 and/or the termination of the electrical stimulation.

Stimulation delivery events 84, 88 indicate times at which electrical stimulation is delivered, and may indicate regular times or irregular times. Therapy trigger event 86 indicates a time that stimulation is terminated to cause the delivery of the post-stimulation, desired therapeutic effect that is observed following such termination of the electrical stimulation. The time period between therapy trigger event 86 and stimulation delivery event 88, when the electrical stimulation is initiated again, may be described as the second time period. During the second time period, stimulation cycle 82 is at substantially zero intensity (e.g., zero intensity or as close to zero as permitted by the hardware of IMD 16) because the electrical stimulation is not being delivered to patient 14 by IMD 16. Although therapy window T may overlap with only a portion of the second time period, as shown in FIG. 4, therapy window T may be equivalent to the second time period in other examples. Generally, the second time period during which stimulation is not delivered, and the post-stimulation, desired therapeutic effect is produced, may be between approximately five minutes and 30 minutes. However, longer or shorter second time periods may be appropriate for some patients or conditions. In the example of FIG. 4, the second time period is approximately 25 minutes, extending from a time of 15 minutes to 40 minutes, relative to event 84 at a time of 0 minutes.

In some examples, the first time period and second time period from one cycle of stimulation cycle 82 may be substantially equal to the first time period and second time period from a subsequent cycle of stimulation cycle 82. In other examples, at least one of the first time period or the second time period may change over subsequent cycles. The changes in time periods may occur due to patient request, clinician instructions, detected physiological states during or after the electrical stimulation, or any other therapeutic reason.

Figure 5:
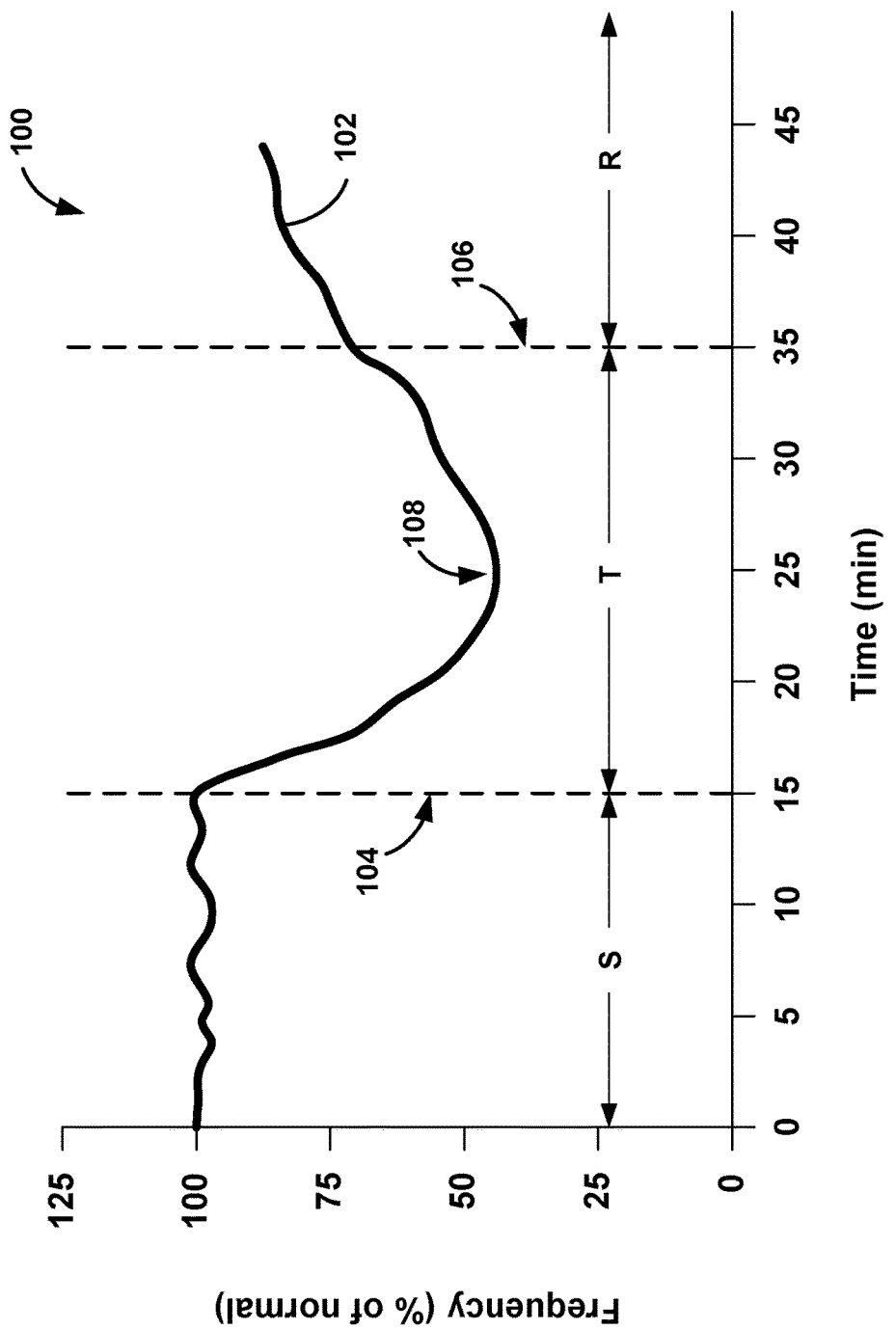
FIG. 5 is an example graph that illustrates a change in bladder contractions after terminating the delivery of a sub-threshold electrical stimulation.

FIG. 5 is an example graph 100 that illustrates an example of a change in the frequency of bladder contractions after terminating the delivery of the electrical stimulation. Graph 100 is shown merely for purposes of illustration of the concept of the post-stimulation therapeutic effect and is not intended to indicate any actual results for any particular patient or patient population. In FIG. 5, frequency 102 is a trace of the bladder contraction frequency of patient 14 over time and may correspond to stimulation cycle 82 and the timeline of FIG. 4. As shown in FIG. 5, frequency 104 is normalized (i.e., divided by) to the bladder contraction frequency observed prior to delivering the electrical stimulation, and frequency 104 changes due to the termination of the electrical stimulation.

When delivery of the electrical stimulation is started at time zero, frequency 102 is approximately equal to 100% of the normalized bladder contraction frequency that exists prior to delivery of stimulation. Hence, in this example, the electrical stimulation does not produce the desired therapeutic effect of reducing the bladder contraction frequency by a desired amount. Over stimulation period S (e.g., the first time period), IMD 16 delivers the electrical stimulation. During stimulation period S, frequency 102 may vary slightly. However, frequency 102 maintains substantially the same bladder contraction frequency as before delivery of the electrical stimulation. In this manner, the electrical stimulation has an intensity that is insufficient to cause the desired therapeutic effect (reduced bladder contraction frequency) during stimulation. In fact, frequency 102 shows substantially zero therapeutic effect on reduction in contraction frequency during stimulation period S, relative to a baseline contraction frequency before delivery of stimulation.

In other examples, frequency 102 may decrease slightly during stimulation period S from the electrical stimulation. However, this change in frequency 102 may only be considered a minimal, ancillary therapeutic effect prior to the termination of stimulation, and may be substantially less than the desired reduction in frequency 102 after stimulation is terminated. For example, the therapeutic efficacy of this ancillary therapeutic effect may be less than 20 percent of the target efficacy level, e.g., for the desired therapeutic effect after termination. In other examples, the minimal therapeutic effect during the electrical stimulation of stimulation period S may be greater than 20% of the desired post-stimulation therapeutic effect after termination. Again, the target efficacy level may correspond to a particular amount of reduction in bladder contractions. In either case, any therapeutic effect or physiological response observed during stimulation period S is not the desired therapeutic effect as specified by a user and may not even be perceived by patient 14.

Hence, in some examples, electrical stimulation is selected to not cause the desired therapeutic effect during stimulation period S, but to cause the desired therapeutic effect after electrical stimulation is terminated. Also, in other examples, the electrical stimulation may be below a physiological threshold that is selected to not cause an acute physiological response, e.g., such as a motor response or patient perception of stimulation, during the stimulation. Again, the intensity of the stimulation may be selected to produce the desired therapeutic effect on a post-stimulation basis. However, in these examples, the intensity is selected to be sub-threshold in the sense that the stimulation does not produce the desired therapeutic effect. To select the intensity in a straightforward manner, a current or voltage amplitude may be selected. However, pulse width, pulse rate or other parameters alternatively or additionally may be select to produce a desired stimulation intensity.

Once therapy trigger event 104 is detected and the electrical stimulation is terminated, bladder contraction frequency 102 may begin to decrease toward a reduced bladder contraction frequency associated with a desired therapeutic effect. The desired therapeutic effect may not occur immediately but may occur at some point during therapy window T. For example, during therapy window T, frequency 102 may decrease steadily until reaching maximum effect 108. Maximum effect 108 may be the maximum therapeutic effect, or part of the desired therapeutic effect, that correlates with the effect of decreased bladder contraction frequency 102. For example, maximum effect 108 may correspond in time to the lowest bladder contraction frequency observed during therapy window T and stimulation period S. However, in some examples, patient 14 may enjoy relief from the bladder dysfunction during all or a majority of therapy window T, e.g., between the 15 and 35 minute marks in graph 100, even though stimulation is not being delivered. In some examples, therapy window T may be coincident with a lockout period during which stimulation is not delivered. As described above, the lockout period may prevent additional stimulation from disrupting the therapy provided during therapy window T. In addition, therapy window T may be equal to the second time period, or at least a portion of the second time period, in which the electrical stimulation is not delivered to patient 14.

After termination of the electrical stimulation and during therapy window T, IMD 16 may start to monitor or continue to monitor physiological states of patient 14. One physiological state may be the bladder contraction frequency indicated by frequency 102. Alternatively, or in addition, IMD 16 may monitor other physiological states to evaluate the effectiveness of the stimulation program used to deliver the electrical stimulation. For example, IMD 16 may monitor potential voiding, bladder pressure, heart rate, breathing rate, or any other physiological responses. IMD 16 may also utilize patient input of perceived efficacy and voiding events, for example, when monitoring post-stimulation therapy. Based on this monitoring, IMD 16 may automatically select new stimulation parameters or a new stimulation program in an attempt to maximize or at least increase the post-stimulation therapeutic effect after subsequent deliveries of the electrical stimulation, i.e., in subsequent stimulation cycles.

Window end 106 may be the time at which the therapy window T ceases. After this time, recovery period R begins and continues as frequency 102 increases back toward the baseline of 100% contraction frequency. Recovery period R may continue for several minutes, hours, or even days. However, IMD 16 may restart the delivery of the subthreshold electrical stimulation at any time during recovery period R. As shown in FIG. 4, for example, IMD 16 may be programmed such that the electrical stimulation may be started again at minute 40, e.g., in a cyclical manner. Alternatively, stimulation may be delivered in an on-demand mode or other modes that are responsive to other therapy trigger events.

Although graph 100 illustrates the bladder contraction frequency as the desired therapeutic effect, other physiological responses may be monitored or targeted by the electrical stimulation as the desired therapeutic effect. For example, the electrical stimulation may be targeted to induce a therapeutic effect on bladder pressure, urinary sphincter pressure, bowel pressure, pelvic pain. In this manner, the post-stimulation therapy may be directed to tissues and areas of patient 14 other than bladder 12.

Figure 6:
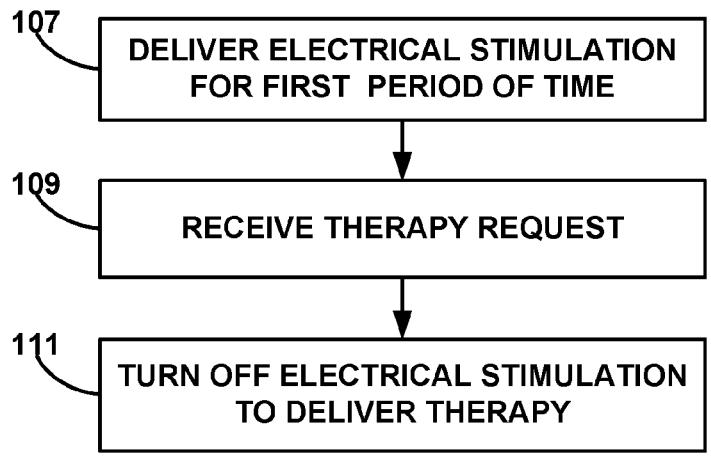
FIG. 6 is a flow diagram that illustrates an example technique for inducing a therapeutic effect by terminating a sub-threshold electrical stimulation.

FIG. 6 is a flow diagram that illustrates an example technique for inducing a desired therapeutic effect by terminating the delivery of electrical stimulation. As described in FIG. 6, control module 50 and stimulation delivery module 52 of IMD 16 may be used to deliver and terminate the electrical stimulation. While FIG. 6 is described with respect to control module 50, in other examples, programmer 24 or other devices may be used to control delivery of electrical stimulation by IMD 16.

In the example of FIG. 6, control module 50 controls stimulation delivery module 52 of IMD 16 to deliver electrical stimulation for a first period of time (107), as described in this disclosure. The electrical stimulation may have an intensity selected that is insufficient to cause the desired therapeutic effect during stimulation delivery but sufficient to induce the desired therapeutic effect after termination of the stimulation. In other words, the delivered stimulation intensity may be below a therapeutic threshold. In other examples, the stimulation may also be below a physiological threshold in that it is selected to have an intensity, e.g., by selection of amplitude, pulse width and/or pulse rate, that is insufficient to cause an acute physiological response, e.g., a motor response or sensory response, during stimulation. As described herein, the stimulation intensity is selected to be sufficient to cause the desired therapeutic effect after termination of the stimulation, at least when the stimulation is applied during a first period of time that is sufficient to cause the desired therapeutic effect after termination of stimulation.

Upon receiving a therapy request (109), such as a therapy trigger event as described in this disclosure (e.g., a patient therapy request, timer expiration, time of day, sensed physiological signal or physiological state determined based on the sensed physiological signal, or characteristic, or the like), control module 50 controls stimulation delivery module 52 of IMD 16 to turn off the electrical stimulation to deliver the therapy (111). In the example shown in FIG. 6, turning off the stimulation causes the desired therapeutic effect, such as reduced bladder contraction frequency. In some examples, the desired therapeutic effect may not be observed or elicited from patient 14 until after the electrical stimulation is turned off or at least reduced to the lowest level permitted by the hardware of IMD 16. Alternatively, the desired therapeutic effect may be provided both during stimulation and after termination of stimulation, in other examples. In each case, stimulation is actually turned off, rather than turned on, to cause the desired therapeutic effect to the patient after termination of the stimulation.

Figure 7:
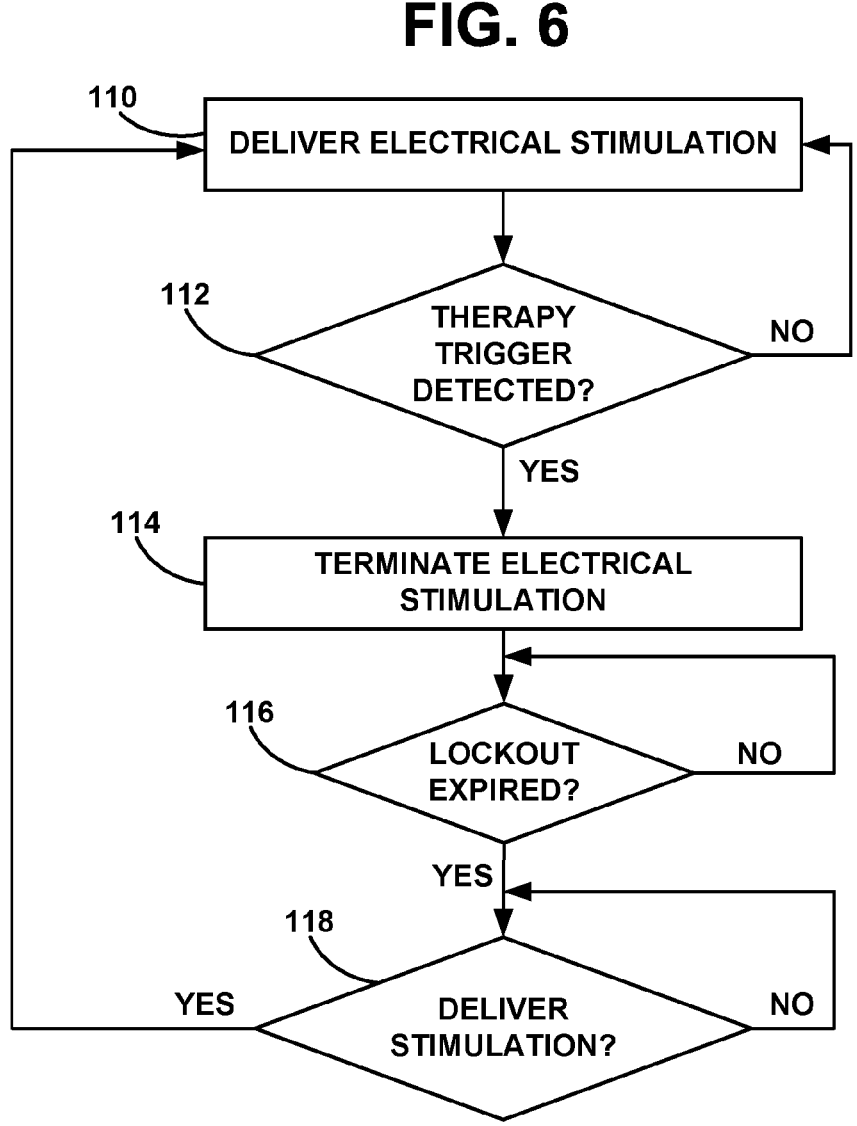
FIG. 7 is a flow diagram that illustrates an example technique for inducing a therapeutic effect by terminating a sub-threshold electrical stimulation.

FIG. 7 is a flow diagram that illustrates an example technique for inducing a therapeutic effect by terminating the electrical stimulation. As described in FIG. 7, control module 50 and stimulation delivery module 52 of IMD 16 may be used to deliver and terminate the electrical stimulation. However, in other examples, programmer 24 or other devices may be used during the control processes.

In the technique shown in FIG. 7, control module 50 controls the delivery of the electrical stimulation with stimulation delivery module 52 (110). As described herein, stimulation may be initiated based on a timer, patient input, detected physiological state, or any other event. As long as the therapy trigger event is not detected ("NO" branch of block 112), stimulation delivery module 52 continues to deliver the electrical stimulation (110). If a therapy trigger event time is known in advance, electrical stimulation may be delivered in advance of the known therapy trigger event to permit sufficient time for the electrical stimulation to cause the desired therapeutic effect after termination of stimulation. The therapy trigger event may be an elapsed time period, e.g., since the end of a previous therapy window, a particular time of day, a patient input requesting therapy, or a detected physiological state, for example.

If control module 50 detects the therapy trigger event ("YES" branch of block 112), then control module 50 terminates the electrical stimulation (114) to cause the post-stimulation therapeutic effect. Although control module 50 may only be configured to detect a single type of therapy trigger event, in other examples, control module 50 may terminate the stimulation upon detecting one of multiple types of therapy trigger event. As one example, termination may occur upon detecting a certain elevated bladder contraction frequency or a patient request for therapy. In some examples, control module 50 may only terminate the electrical stimulation after detecting two sequential therapy trigger events (e.g., an expiration of a timer and a subsequent patient input request for therapy).

Once stimulation is terminated, control module 50 enters the second time period, or therapy window, in which the desired therapeutic effect is induced. During this time, control module 50 may be subject to a lockout period. If the lockout period has not expired ("NO" branch of block 116), control module 50 is still prevented from delivering stimulation. Once the lockout period expires ("YES" branch of block 116), control module 50 checks to determine if the electrical stimulation is to be delivered again (118). For example, control module 50 may determine stimulation is to be delivered again (e.g., for another first period of time) based on a continued request from the patient, a physiological state exceeding a threshold, or any other condition in which stimulation is to be delivered. If no stimulation is to be delivered ("NO" branch of block 118), control module 50 does not deliver stimulation. If control module 50 receives a command to deliver electrical stimulation ("YES" branch of block 118), then control module 50 controls stimulation delivery module 52 to deliver the electrical stimulation again (110).

As described herein, the lockout period may be at least a portion of the therapy window and/or the second time period between delivery of the electrical stimulation. The lockout period may essentially be a first event that needs to occur before another command for stimulation is received. In examples in which the electrical stimulation is delivered only based on timers or schedules, the lockout period may not be necessary.

As discussed above, in various implementations, the electrical stimulation may be continuously delivered and terminated in response to a therapy trigger event to cause the desired therapeutic event post-stimulation, i.e., after termination of the stimulation. Alternatively, the electrical stimulation may be initiated at some sufficient period of time in advance of a known therapy trigger event, particularly where the electrical stimulation must be delivered for a minimum period of time to support generation of the desired therapeutic effect after termination of stimulation. In other examples, if electrical stimulation is not already being delivered and must be delivered for some period of time, the electrical stimulation may be initiated in response to the trigger therapy event, such a patient therapy request or detection of a physiological signal, and then terminated after the electrical stimulation has been delivered for at least a minimum period of time sufficient to support the post-stimulation, desired therapeutic effect.

Figure 8:
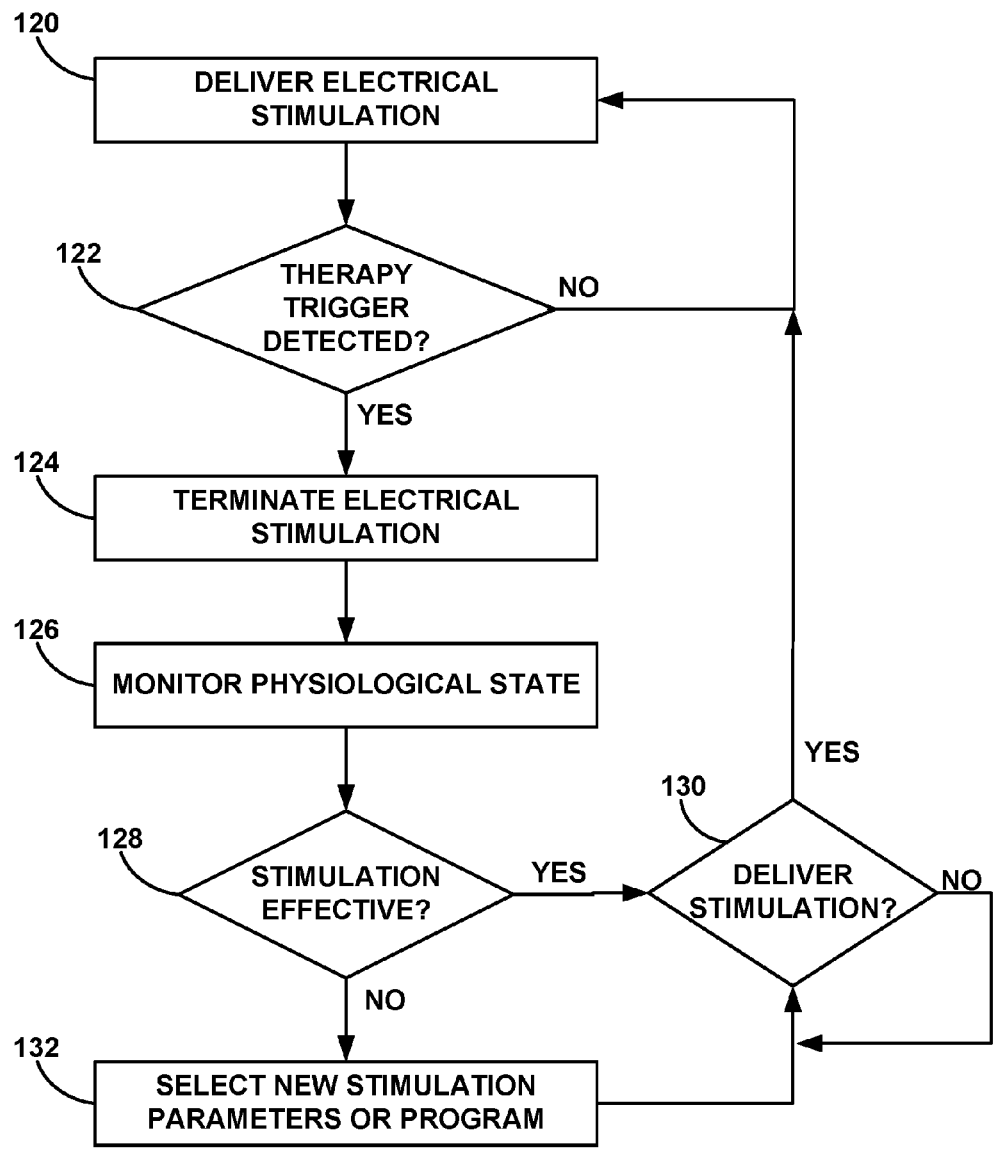
FIG. 8 is a flow diagram that illustrates an example technique for monitoring a physiological state to adjust parameters of a sub-threshold electrical stimulation.

FIG. 8 is a flow diagram that illustrates an example technique for monitoring a physiological state to adjust parameters of an electrical stimulation. As described in FIG. 8, control module 50 and stimulation delivery module 52 of IMD 16 may be used to deliver and terminate the electrical stimulation. Control module 50 may also automatically select new parameters. However, in other examples, programmer 24 or other devices may be used during technique of FIG. 8.

Control module 50 initially controls the delivery of the electrical stimulation with stimulation delivery module 52 (120). As long as the therapy trigger event is not detected ("NO" branch of block 122), stimulation delivery module 52 continues to deliver the electrical stimulation (120). If control module 50 detects the therapy trigger event ("YES" branch of block 122), then control module 50 terminates the electrical stimulation (124).

Once stimulation is terminated, control module 50 enters the second time period, or therapy window, in which the therapeutic effect is induced. During this time, control module 50 may monitor one or more physiological states of patient 14 (126). For examples, control module 50 may monitor changes to the bladder contraction frequency, bladder pressure, nerve signals, or even patient 14 input for any responses indicative of a post-stimulation induced therapeutic effect. Based on this monitoring, control module 50 may determine if the electrical stimulation was effective at inducing a therapeutic effect (128). In some examples, control module 50 may determine effectiveness based on one or more thresholds for the physiological states (e.g., bladder contraction frequency or bladder pressure) monitored after stimulation termination. If the electrical stimulation was effective ("YES" branch of block 128), control module 50 continues to determine when to again deliver the electrical stimulation (130), e.g., upon the start of another therapy cycle in advance of a known therapy trigger event or in response to a therapy trigger event. Alternatively, if the electrical stimulation was effective, control module 50 may return to continuously deliver stimulation (120), possibly after some time delay, and wait for the next therapy trigger event.

If the electrical stimulation was not effective ("NO" branch of block 128), then control module 50 may select new stimulation parameters or new stimulation programs that define the electrical stimulation (132). Control module 50 may follow parameter or program selection rules stored in memory 56. In one example, control module 50 may simply select the next program in a list of ordered programs provided by the clinician. In another example, control module 50 may refer to a lookup table that indicates certain parameters or programs to try based on the physiological states monitored after termination of the stimulation. In some examples, control module 50 may continue to adhere to staying below the therapeutic intensity threshold, or the threshold stimulation intensity for sub-threshold stimulation, when adjusting stimulation parameters and programs.

After the parameters of the electrical stimulation have been adjusted, control module 50 determines when to again deliver the electrical stimulation (130). Once control module 50 determines that electrical stimulation is to be delivered ("YES" branch of block 130), control module 50 controls stimulation delivery module 52 to deliver the electrical stimulation (120).

In other examples, control module 50 may not directly select new stimulation parameters or programs. Instead, control module 50 may transmit a request to programmer 24 that new stimulation parameters or programs are required. Programmer 24 may then prompt the user, e.g., a clinician or patient 14, to select new stimulation parameters or new stimulation programs to control the delivery of the electrical stimulation. Programmer 24 may also present any associated physiological data and patient input data indicating that a modification to the electrical stimulation may be appropriate.

Delivery of electrical stimulation for a first period of time to cause a desired therapeutic effect after termination of stimulation for a second period of time may be achieved using a variety of different parameters. The electrical stimulation may be delivered with an intensity sufficient to cause a desired therapeutic effect at time after termination of the stimulation, but insufficient to cause an acute therapeutic responses during stimulation. Alternatively, the sub-threshold stimulation may be delivered with an intensity sufficient to cause a desired therapeutic effect after termination of the stimulation, but insufficient to cause an acute physiological response during stimulation.

As one example, the electrical stimulation for inducing a desired post-stimulation therapeutic effect may have a current amplitude of approximately 0.1 mA to approximately 20 mA, a pulse width of approximately 10 microseconds to approximately 1000 microseconds, and a pulse rate of approximately 0.5 Hz to approximately 500 Hz, delivered for a period of approximately 2 minutes to approximately 30 minutes, to, such as a current amplitude of 0.1 mA to 20 mA, a pulse width of 10 microseconds to 1000 microseconds, and a pulse rate of 0.5 Hz to 500 Hz, delivered for a period of 2 minutes to 30 minutes, to be effective in producing a desired therapeutic effect of a substantial reduction of bladder contraction frequency after stimulation is terminated.

As another example, electrical stimulation having a current amplitude of approximately 0.5 mA to approximately 10 mA, a pulse width of approximately 100 microseconds to approximately 500 microseconds, and a pulse rate of approximately 1.0 Hz to approximately 250 Hz, delivered for a period of approximately 5 to approximately 20 minutes, may be effective in producing a desired therapeutic effect of a substantial reduction of bladder contraction frequency after stimulation is terminated. As a further example, electrical stimulation having a current amplitude of approximately 1.0 Hz to approximately 10 mA, a pulse width of approximately 200 microseconds to approximately 300 microseconds, and a pulse rate of approximately 1.0 Hz to approximately 20 Hz, delivered for a period of approximately 10 minutes to approximately 20 minutes, may be effective in producing a desired therapeutic effect of a substantial reduction of bladder contraction frequency after stimulation is terminated. Depending upon the subject, one or more of these example stimulation parameters may also be sufficient to generate sub-threshold electrical stimulation.

Example

FIG. 9 is a graph that illustrates a change in bladder contraction frequency in response to electrical stimulation and post-stimulation therapeutic effect for different durations of stimulation delivered to rat test subjects. The y-axis labeled "Frequency (normalized %)" indicates a frequency of bladder contractions during electrical stimulation relative to the frequency of bladder contractions before electrical stimulation was applied. In order to determine the "Frequency (normalized %)," bladder contraction frequencies during electrical stimulation were normalized by dividing bladder contraction frequencies during electrical stimulation by a control frequency for the rat test subject, the control frequency being the bladder contraction frequency observed prior to delivery of any electrical stimulation.

The results in the graph of FIG. 9 illustrate that lower intensities of electrical stimulation (e.g., intensities that are insufficient to cause a desired therapeutic effect during stimulation but sufficient to cause the desired therapeutic effect after termination of stimulation) delivered to the spinal nerve of the rat test subject for approximately 10 minutes and 20 minutes (but not approximately 2 minutes and 5 minutes) inhibited bladder rhythmic contraction in rats. Maximal inhibition of bladder contractions appeared approximately 10 minutes after termination of stimulation, i.e., post-stimulation. In contrast, there were no acute therapeutic responses to the lower intensity neurostimulation during the stimulation periods. Additionally, higher intensity stimulations of a duration of approximately 10 minutes induced an acute quieting response of the bladder contractions, as well as a longer term, post-stimulation response.

The experimental results shown in FIG. 9 indicate that termination of electrical stimulation may induce urinary bladder quieting, i.e., reduction in bladder contraction frequency, such that termination of electrical stimulation may be used to configure electrical stimulation therapy for bladder dysfunction. The ON phase duration of electrical stimulation may be at least approximately 10 minutes, which may be followed by an OFF phase. The stimulation may be insufficient to cause the desired therapeutic effect during stimulation. The therapeutic effect of this stimulation cycling may be measurable as long term modulation of a neural or other physiological response after stimulation is terminated, and not necessarily as an acute physiological response during stimulation. Wider applications to other neural systems and therapies may be provided.

The data illustrated in the graph of FIG. 9 was obtained from a plurality of tests performed on Sprague-Dawley female laboratory rats weighing approximately 200 grams (g) to approximately 300 g. To record bladder contractions, a cannula (a PE 50—polyethylene cannula, e.g., having a 0.58 mm inner diameter) was placed into the bladder of each test subject via the urethra which was ligated to create an isovolumetric bladder. The urethral cannula was connected via a T-type connector (e.g., a three terminal connector) to a low volume pressure transducer of a data acquisition system. The other end of the T-type connector was linked to a 20 cubic centimeter (cc) syringe with a perfusion pump.

To deliver electrical stimulation, a wire electrode was placed bilaterally under the L6 spinal nerve of the test subject. The dorsal skin around the sacral and thoracic surface of the test subject was shaved and a dorsal midline incision was made from approximately spinal nerve L3 to S2. The L6/S1 posterior processes were exposed. The S1 processes were removed and the L6 nerve trunks localized caudal and medial to the sacroiliac junction. After the wire electrode was placed under each nerve with two bared portions of Teflon-coated, 40-guage, stainless steel wire, silicone adhesive was applied to cover the wire around the nerve, and sutured shut. The wire electrode was connected to a stimulus isolator (an SIU-V Grass Medical Instruments Stimulus Isolation Unit available from Astro-Med, Inc of West Warwick, R.I.) with a Grass S88 stimulator. A needle electrode under the skin of the tail of the test subject served as the ground. The stimulator generated pulses to both nerves serially.

To induce rhythmic bladder contractions, saline was infused into the bladder of the test subject at a rate of approximately 50 microliters per minute (μL/minute) to induce a micturition reflex (defined here as bladder contraction with intensity >10 millimeters of mercury (mmHg)). The infusion rate was then lowered to approximately 10 μL per minute until 3-5 consecutive contractions were established. Infusion was then terminated.

In general, FIG. 9 shows effects of different stimulation durations of spinal nerve stimulation on isovolumetric bladder contractions. In summary, electrical stimulation for approximately 10 minutes and 20 minutes induced post-stimulation bladder-quieting responses (i.e., contract frequency reductions) to stimulation for approximately 10 to 20 minutes (p<0.05, two-way ANOVA). The key in FIG. 9 illustrates the number of rats (n) tested for each condition. By considering two factors (inhibitory effects to different time points in control and stimulated rats), the inhibitory effects by stimulation is statistically significant. Such analysis has been tested by 2-way ANOVA. The null hypothesis is that stimulation does not affect the bladder contractions, and p<0.05 indicates that there is less than 5% chance that the null hypothesis is true. This statistically significant indication has been made for when electrical stimulation of approximately 10 minutes and 20 minutes induced post-stimulation bladder-quieting responses. Such results were repeatable in many rats, as indicated by the n value. For example, 8 rats, 7 rats, 7 rats, 11 rats, and 9 rats were tested with electrical stimulation for 1 minute, 2 minutes, 5 minutes, 10 minutes, and 20 minutes, respectively.

During the tests, bladder contractions of one or more test subjects were observed during a period prior to, during, and after stimulation (labeled in FIG. 9 as −15 min to 20 min). During observation, the test subject was provided with electrical stimulation (to a spinal nerve) for different durations of time. The data in FIG. 9 has been adjusted so that the entire duration of stimulation is represented as a single point, at "Stim" along the x-axis of FIG. 9. In addition, box 140 indicates the point in time of the electrical stimulation delivery for each group. This allows the onset and offset of the respective stimulation periods to be aligned in FIG. 9. For each test run (i.e., each observation period), a frequency of bladder contractions was determined at approximately 5 minute intervals. The determined frequencies of bladder contractions were then normalized (i.e., divided by) by a frequency of bladder contractions of the test subject at −5 minutes. The normalized bladder contraction frequencies are graphed in FIG. 9.

The duration of the stimulation period delivered to the test subject is indicated by the shape of the data point. The open-circle data points indicate measurement of contractions in subjects that did not receive electrical stimulation (the control group). Accordingly, the open-circle data points are equal to approximately 100% normalized frequency. The diamond data points indicate measurement of contractions in subjects that received stimulation for about 2 minutes. The stimulation indicated by the diamond data points was delivered as continuous pulses at a frequency (i.e., pulse rate) of 10 Hz, a pulse width of 100 μs, and an amplitude that resulted at approximately the threshold stimulation intensity for each test subject (e.g., the mean current pulse amplitude for the stimulation was about 0.21 mA). As described in this disclosure, the physiological threshold stimulation intensity is the stimulation intensity at which stimulation causes a certain acute physiological response, e.g., a motor threshold, a stimulation perception threshold, a non-therapeutic effect, or a detected physiological response, such as nerve action potentials. In the example of FIG. 9, the current amplitude was selected such that the stimulation intensity met the motor threshold intensity that induced an acute motor response, i.e., muscle twitch in the example of FIG. 9, in the subject. However, this stimulation intensity was insufficient to cause the desired therapeutic effect during stimulation delivery.

The downward-oriented triangle data points (i.e., the triangles with points oriented downward) indicate measurement of contractions in subjects that received stimulation for about 5 minutes. The stimulation indicated by the downward triangle data points was delivered at a frequency of 10 Hz and an amplitude that resulted in the physiological threshold stimulation intensity for each test subject (mean of about 0.21 mA). The upward-oriented triangle data points (i.e., the triangles with points oriented upward) indicate measurement of contractions in subjects that received stimulation for about 10 minutes. The stimulation indicated by the upward triangle data points was delivered at a frequency of 10 Hz and an amplitude that resulted in the physiological threshold stimulation intensity for each test subject (mean of about 0.16 mA).

The closed-circle data points indicate measurement of contractions in subjects that received stimulation for about 20 minutes. The stimulation indicated by the closed-circle data points was delivered at a frequency of 10 Hz and an amplitude that resulted in the physiological threshold stimulation intensity for each test subject (mean of about 0.21 mA). Each of the data points includes a standard deviation bar to indicate the amount of variation between measurements. The standard deviation bars, e.g., illustrated in one example as standard deviation bar 142, are included to indicate the standard deviation between measurements used to produce each data point.

With respect to the downward-oriented triangle data points and the diamond data points, the stimulation caused substantially no change in the bladder contraction frequency, either during or after stimulation.

With respect to the closed-circle data points and the upward-oriented triangle data points, the stimulation may have provided some inhibition of bladder contraction frequency during the time when stimulation was provided (20 minutes and 10 minutes, respectively). Additionally, the 10-minute and 20-minute stimulations each elicited a greater inhibition of bladder contraction frequency after the stimulation was terminated. For example, about 10 minutes after stimulation was terminated (i.e., at the 10 minute mark), the bladder contraction frequency was reduced to between about 40% and about 60% of the control frequency for each of the 10-minute stimulation and the 20-minute stimulation. Accordingly, FIG. 9 illustrates that relatively low intensity stimulation at a frequency of about 10 Hz may elicit a greater physiological response after stimulation is terminated than when the stimulation is being delivered to the patient. Little to no physiological response was detected during the delivery of stimulation within box 140.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by control module 50 of IMD 16 and/or control module 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The invention claimed is:

1. A system comprising:
   a stimulation generator configured to generate and deliver electrical stimulation to a patient; and
   processing circuitry configured to:
      control the stimulation generator to deliver the electrical stimulation to the patient;
      detect a therapy trigger event;
      responsive to detecting the therapy trigger event, control the stimulation generator to terminate the delivery of the electrical stimulation;
      responsive to controlling termination of the delivery of the electrical stimulation, determine whether termination of the electrical stimulation induced a desired therapeutic effect in the patient, wherein the desired therapeutic effect comprises a decrease in bladder dysfunction; and
      control the stimulation generator based on the determination of whether termination of the electrical stimulation induced the desired therapeutic effect in the patient.

2. The system of claim 1, wherein the processing circuitry is configured to:
   determine whether termination of the electrical stimulation induced the desired therapeutic effect in the patient by at least:
      determining that a physiological state of the patient changed after termination of the electrical stimulation; and
      responsive to determining that the physiological state of the patient changed after termination of the electrical stimulation, determining that termination of the electrical stimulation induced the desired therapeutic effect in the patient; and
   control the stimulation generator by, responsive to determining that termination of the electrical stimulation induced the desire therapeutic effect in the patient, controlling the stimulation generator to subsequently control the stimulation generator to deliver the electrical stimulation to the patient and controlling the stimulation generator to terminate the delivery of the electrical stimulation to induce the desired therapeutic effect in the patient.

3. The system of claim 2, wherein the processing circuitry is configured to determine that the physiological state of the patient changed after termination of the electrical stimulation by at least determining that a sensed value of a physiological parameter exceeds a threshold.

4. The system of claim 2, further comprising a sensor configured to sense a physiological parameter indicative of the physiological state.

5. The system of claim 2, wherein the physiological state comprises at least one of a bladder pressure, a bladder contraction frequency, a nerve activity, a muscle activity, a patient activity level, or a patient posture state.

6. The system of claim 1, wherein the electrical stimulation is a first electrical stimulation at least partially defined by a first set of stimulation parameter values, and wherein the processing circuitry is configured to:
   determine whether termination of the first electrical stimulation induced a desired therapeutic effect in the patient by at least determining that a physiological state of the patient did not change after termination of the first electrical stimulation, the physiological state not changing being indicative of the desired therapeutic effect not being induced by termination of the first electrical stimulation, and
   control the stimulation generator by, responsive to determining that the physiological state of the patient did not change, selecting a second set of stimulation parameter values that at least partially defines a second electrical stimulation deliverable to the patient and is configured to induce the desired therapeutic effect in the patient after termination of delivery of the second electrical stimulation, the second set of stimulation parameter values being different than the first set of stimulation parameter values.

7. The system of claim 6, wherein the processing circuitry is configured to select the second set of stimulation parameter values based on a next therapy program in a list of ordered therapy programs stored in a memory.

8. The system of claim 6, wherein the processing circuitry is configured to select the second set of stimulation parameter values based on a lookup table that indicates one or more parameter values to try based on the physiological state determined after termination of the first electrical stimulation.

9. The system of claim 1, wherein the therapy trigger event comprises at least one of an expiration of a timer, a particular time of day, or a detected physiological state of the patient.

10. The system of claim 1, wherein the therapy trigger event comprises a request by a user for the desired therapeutic effect.

11. The system of claim 1, wherein the electrical stimulation comprises an intensity that is below an intensity of at least one of a therapeutic threshold or a physiological threshold of the patient.

12. The system of claim 1, wherein the desired therapeutic effect comprises at least one of a reduced bladder contraction frequency, a reduced urgency, or reduced incontinence.

13. A method comprising:
   controlling, by processing circuitry, a stimulation generator to generate and deliver electrical stimulation to a patient;
   detecting, by the processing circuitry, a therapy trigger event;

responsive to detecting the therapy trigger event, controlling, by the processing circuitry, the stimulation generator to terminate the delivery of the electrical stimulation;

responsive to controlling termination of the delivery of the electrical stimulation, determining, by the processing circuitry, whether the termination of the electrical stimulation induced a desired therapeutic effect in the patient, wherein the desired therapeutic effect comprises a decrease in bladder dysfunction; and controlling, by the processing circuitry, the stimulation generator based on the determination of whether termination of the electrical stimulation induced the desired therapeutic effect in the patient.

14. The method of claim 13, wherein:

determining whether the termination of the electrical stimulation induced the desired therapeutic effect in the patient comprises:

determining that a physiological state of the patient changed after termination of the electrical stimulation; and responsive to determining that the physiological state of the patient changed after termination of the electrical stimulation, determining that termination of the electrical stimulation induced the desired therapeutic effect in the patient; and controlling the stimulation generator comprises, responsive to determining that termination of the electrical stimulation induced the desire therapeutic effect in the patient, controlling the stimulation generator to subsequently control the stimulation generator to deliver the electrical stimulation to the patient and controlling the stimulation generator to terminate the delivery of the electrical stimulation to induce the desired therapeutic effect in the patient.

15. The method of claim 14, wherein determining that the physiological state of the patient changed after termination of the electrical stimulation comprises determining that a sensed value of a physiological parameter exceeds a threshold.

16. The method of claim 14, further comprising sensing a physiological parameter indicative of the physiological state.

17. The method of claim 13, wherein the electrical stimulation is a first electrical stimulation at least partially defined by a first set of stimulation parameter values, and wherein determining whether the termination of the electrical stimulation induced a desired therapeutic effect in the patient comprises:

determining whether termination of the first electrical stimulation induced a desired therapeutic effect in the patient comprises determining that a physiological state of the patient did not change after termination of the first electrical stimulation, the physiological state not changing being indicative of the desired therapeutic effect not being induced by termination of the first electrical stimulation; and controlling the stimulation generator comprises, responsive to determining that the physiological state of the patient did not change, selecting a second set of stimulation parameter values that at least partially defines a second electrical stimulation deliverable to the patient and is configured to induce the desired therapeutic effect in the patient after termination of delivery of the second electrical stimulation, the second set of stimulation parameter values being different than the first set of stimulation parameter values.

18. The method of claim 17, wherein selecting the second set of stimulation parameter values comprises selecting the second set of stimulation parameter values based on a next therapy program in a list of ordered therapy programs stored in a memory.

19. The method of claim 17, wherein selecting the second set of stimulation parameters comprises selecting the second set of stimulation parameters based on a lookup table that indicates one or more parameters to try based on the physiological state determined after termination of the first electrical stimulation.

20. The method of claim 13, wherein the therapy trigger event comprises at least one of an expiration of a timer, a particular time of day, or a detected physiological state of the patient.

21. The method of claim 13, wherein the therapy trigger event comprises a request by a user for the desired therapeutic effect.

22. The method of claim 13, wherein the electrical stimulation comprises an intensity that is below an intensity of at least one of a therapeutic threshold or a physiological threshold of the patient.

23. The method of claim 13, wherein the desired therapeutic effect comprises at least one of a reduced bladder contraction frequency, a reduced urgency, or reduced incontinence.

24. A system comprising:

means for delivering electrical stimulation to a patient;

means for detecting a therapy trigger event;

means for, responsive to detecting the therapy trigger event, controlling the means for delivering electrical stimulation to terminate the delivery of the electrical stimulation;

means for, responsive to controlling termination of the delivery of the electrical stimulation, determining whether the termination of the electrical stimulation induced a desired therapeutic effect in the patient, wherein the desired therapeutic effect comprises a decrease in bladder dysfunction; and means for controlling the means for delivering electrical stimulation based on the determination of whether termination of the electrical stimulation induced the desired therapeutic effect in the patient.

\* \* \* \* \*